(12) United States Patent
Deisseroth et al.

(10) Patent No.: US 11,531,035 B2
(45) Date of Patent: Dec. 20, 2022

(54) CALCIUM INDICATOR POLYPEPTIDES AND METHODS OF USE THEREOF

(71) Applicant: The Board of Trustees of the Leland Stanford Junior University, Stanford, CA (US)

(72) Inventors: Karl A. Deisseroth, Stanford, CA (US); Charu Ramakrishnan, San Jose, CA (US); Masatoshi Inoue, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 236 days.

(21) Appl. No.: 15/990,132

(22) Filed: May 25, 2018

(65) Prior Publication Data

US 2018/0372762 A1    Dec. 27, 2018

Related U.S. Application Data

(60) Provisional application No. 62/523,048, filed on Jun. 21, 2017.

(51) Int. Cl.
| | |
|---|---|
| *G01N 33/84* | (2006.01) |
| *C07K 14/47* | (2006.01) |
| *G01N 33/58* | (2006.01) |
| *G01N 33/50* | (2006.01) |
| *G01N 33/542* | (2006.01) |
| *C07K 14/705* | (2006.01) |

(52) U.S. Cl.
CPC .......... *G01N 33/84* (2013.01); *C07K 14/4728* (2013.01); *C07K 14/705* (2013.01); *G01N 33/5041* (2013.01); *G01N 33/542* (2013.01); *G01N 33/582* (2013.01); *C07K 2319/60* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 2016/0176931 A1* | 6/2016 | Kim ................. | A01K 67/0275 424/9.6 |
| 2017/0016912 A1 | 1/2017 | Huang | |

OTHER PUBLICATIONS

Barykina, et al.; "A new design for a green calcium indicator with a smaller size and a reduced number of calcium-binding sites"; Scientific Reports; vol. 6, No. 34447, pp. 15 pages (Sep. 28, 2016).
Dana, et al.; "Sensitive red protein calcium indicators for imaging neural activity"; eLIFE; vol. 5, 24 pages (Mar. 24, 2016).
Heim, et al.; "Genetically Encoded Indicators of Cellular Calcium Dynamics Based on Troponin C and Green Fluorescent Protein"; The Journal of Biological Chemistry; vol. 279, No. 14, pp. 14280-14286 (2004).
Palmer, et al.; "$Ca^{2+}$ Indicators Based on Computationally Redesigned Calmodulin-Peptide Pairs"; Chemistry & Biology; vol. 13, pp. 521-530 (May 2006).
Piccirillo, et al.; "An unconventional dileucine-based motif and a novel cytosolic motif are required for the lysosomal and melanosomal targeting of OA1"; J. Cell Sci.; vol. 119, Pt 10, pp. 2003-2014 (May 15, 2006).
Zhao, et al.; "An Expanded Palette of Genetically Encoded $Ca^{2+}$ Indicators"; Science; vol. 333, No. 6051, pp. 1888-1891 (Sep. 30, 2011).
Zhao, et al.; "An Expanded Palette of Genetically Encoded $Ca^{2+}$ Indicators"; Science; vol. 333, No. 6051, pp. 1888-1891 (Sep. 30, 2011). [Supplemental Material].

\* cited by examiner

*Primary Examiner* — Sergio Coffa
(74) *Attorney, Agent, or Firm* — Rudy J. Ng; Paula A. Borden; Bozicevic, Field & Francis LLP

(57) ABSTRACT

The present disclosure provides a genetically encoded calcium indicator (GECI), nucleic acids encoding the GECI, and host cells comprising the GECI. The present disclosure also provides methods of detecting a change in the intracellular concentration of a cell expressing a GECI of the present disclosure.

18 Claims, 16 Drawing Sheets

Specification includes a Sequence Listing.

FIG. 1 sRGECO — M13 — mApple(146-231) — mApple(6-145) — CaM

**MVDSSRRKWNKAGHAVRAIGRLSSPVVSERMYPEDGALKSEIKKGLRLKDGGHYAAEVKTTYKA
KKPVQLPGAYIVDIKLDIVSHNEDYTIVEQCERAEGRHSTGGMDELYKGGTGGSLVSKGEEDNM
AII**KEFMRFKVHMEGSVNGHEFEIEGEGEGRPYEAFQTAKLKVTKGGPLPFAWDILSPQFMYGS
KAYIKHPADIPDYFKLSFPEGFRWDRVMNFEDGGIIHVNQDSSLQDGVFIYKVKLRGTNFPPDG
PVMQKKTMGWEATRDDLTEEQIAEFKEAFSLFDKDGDGTITTKELGTVFRSLGQNPTEAELQDM
INEVDADGDGTFDFPEFLTMMARKMNDTDSEEEIREAFRVFDKDGNGYIGAAELRHVMTDLGEK
LTDEEVDEMIRVADIDGDGQVNYEEFVQMMTAK (SEQ ID NO:1)

FIG. 2 jRGECO1a — M13 — mApple(146-231) — mApple(6-145) — CaM

**MGSHHHHHHGMASMTGGQQMGRDLYDDDDKDLATMVDSSRRKWNKAGHAVRAIGRLSSPVVSER
MYPEDGALKSEIKKGLRLKDGGHYAAEVKTTYKAKKPVQLPGAYIVDIKLDIVSHNEDYTIVEQ
CERAEGRHSTGGMDELYKGGTGGSLVSKGEEDNMAII**KEFMRFKVHMEGSVNGHEFEIEGEGEG
RPYEAFQTAKLKVTKGGPLPFAWDILSPQFMYGSKAYIKHPADIPDYFKLSFPEGFRWERVMNF
EDGGIIHVNQDSSLQDGVFIYKVKLRGTNFPPDGPVMQKKTMGWEATRDDLTEEQIAEFKEAFS
LFDKDGDGTITTKELGTVFRSLGQNPTEAELQDMINEVDADGDGTFDFPEFLTMMARKMNDTDS
EEEIREAFRVFDKDGNGYIGAAELRHVMTDLGEKLTDEEVDEMIRVADIDGDGQVNYEEFVQMM
TAK (SEQ ID NO:2)

FIG. 6

(Depolarizing opsins)

Amino acid sequence of ChR2 (SEQ ID NO:37)

MDYGGALSAVGRELLFVTNPVVVNGSVLVPEDQCYCAGWIESRGTNGAQTASNVLQWLAAGFSILLLMFYAYQTWK
STCGWEEIYVCAIEMVKVILEFFFEFKNPSMLYLATGHRVQWLRYAEWLLTCPVILIHLSNLTGLSNDYSRRTMGLLVSDI
GTIVWGATSAMATGYVKVIFFCLGLCYGANTFFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIRKTTKLNIGGTEIEVETLVEDEAEAGAVP

Amino acid sequence of ChR2 with ER export and trafficking signal sequences (SEQ ID NO:38)

MDYGGALSAVGRELLFVTNPVVVNGSVLVPEDQCYCAGWIESRGTNGAQTASNVLQWLAAGFSILLLMFYAYQTWK
STCGWEEIYVCAIEMVKVILEFFFEFKNPSMLYLATGHRVQWLRYAEWLLTCPVILIHLSNLTGLSNDYSRRTMGLLVSDI
GTIVWGATSAMATGYVKVIFFCLGLCYGANTFFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIRKTTKLNIGGTEIEVETLVEDEAEAGAVP*AAA***KSR
ITSEGEYIPLDQIDINV**FCYENEV amino acid sequence of a ChR2 SSFO (SEQ ID NO:39)

MDYGGALSAVGRELLFVTNPVVVNGSVLVPEDQCYCAGWIESRGTNGAQTASNVLQWLAAGFSILLLMFYAYQTWK
STCGWEEIYVCAIEMVKVILEFFFEFKNPSMLYLATGHRVQWLRYAEWLLTSPVILIHLSNLTGLSNDYSRRTMGLLVSAI
GTIVWGATSAMATGYVKVIFFCLGLCYGANTFFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIRKTTKLNIGGTEIEVETLVEDEAEAGAVP amino acid sequence of a ChR2 SSFO with ER export and trafficking signal sequences (SEQ ID NO:40)

MDYGGALSAVGRELLFVTNPVVVNGSVLVPEDQCYCAGWIESRGTNGAQTASNVLQWLAAGFSILLLMFYAYQTWK
STCGWEEIYVCAIEMVKVILEFFFEFKNPSMLYLATGHRVQWLRYAEWLLTSPVILIHLSNLTGLSNDYSRRTMGLLVSAI
GTIVWGATSAMATGYVKVIFFCLGLCYGANTFFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIRKTTKLNIGGTEIEVETLVEDEAEAGAVP*AAA***KSR
ITSEGEYIPLDQIDINV**FCYENEV

FIG. 6 (Cont.)

Amino acid sequence of a VChR1 (SEQ ID NO:41)

Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed

Amino acid sequence of a VChR1 with ER export and trafficking signal sequences
(SEQ ID NO:42)

Mdypvarslivryptdlgngtvcmprgqcycegwlrsrgtsiektiaitlqwvvfalsvaclgw
yayqawratcgweevyvaliemmksiieafhefdspatlwlssgngvvwmrygewlltcpvlli
hlsnltglkddyskrtmgllvsdvgcivwgatsamctgwtkilfflislsygmytyfhaakvyi
eafhtvpkgicrelvrvmawtffvawgmfpvlfllgtegfghispygsaighsildliaknmwgvl
gnylrvkihehillygdirkkqkitiagqemevetlvaeeed*AAA*KSRITSEGEYIPLDQIDINVFCY
ENEV amino acid sequence of C1V1 (SEQ ID NO:43)

MSRRPWLLALALAVALAAGSAGASTGSDATVPVATQDGPDYVFHRAHERMLFQTSYTLENNGSVICIPNNGQCFCL
AWLKSNGTNAEKLAANILQWITFALSALCLMFYGYQTWKSTCGWEEIYVATIEMIKFIIEYFHEFDEPAVIYSSNGNKT
VWLRYAEWLLTCPVLLIHLSNLTGLKDDYSKRTMGLLVSDVGCIVWGATSAMCTGWTKILFFLISLSYGMYTYFHAAK
VYIEAFHTVPKGICRELVRVMAWTFFVAWGMFPVLFLLGTEGFGHISPYGSAIGHSILDLIAKNMWGVLGNYLRVKIH
EHILLYGDIRKKQKITIAGQEMEVETLVAEEED amino acid sequence of C1V1 with ER export and trafficking signal sequences
(SEQ ID NO:44)

MSRRPWLLALALAVALAAGSAGASTGSDATVPVATQDGPDYVFHRAHERMLFQTSYTLENNGSVICIPNNGQCFCL
AWLKSNGTNAEKLAANILQWITFALSALCLMFYGYQTWKSTCGWEEIYVATIEMIKFIIEYFHEFDEPAVIYSSNGNKT
VWLRYAEWLLTCPVLLIHLSNLTGLKDDYSKRTMGLLVSDVGCIVWGATSAMCTGWTKILFFLISLSYGMYTYFHAAK
VYIEAFHTVPKGICRELVRVMAWTFFVAWGMFPVLFLLGTEGFGHISPYGSAIGHSILDLIAKNMWGVLGNYLRVKIH
EHILLYGDIRKKQKITIAGQEMEVETLVAEEED*AAA*KSRITSEGEYIPLDQIDINVFCYENEV

FIG. 6 (Cont.)

Amino acid sequence of a C1C2 (SEQ ID NO:45)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAV

Amino acid sequence of a C1C2 with ER export and trafficking signal sequences (SEQ ID NO:46)

MSRRPWLLALALAVALAAGSAGASTGSDATVPVATQDGPDYVFHRAHERMLFQTSYTLENNGSVICIPNN
GQCFCLAWLKSNGTNAEKLAANILQWITFALSALCLMFYGYQTWKSTCGWEEIYVATIEMIKFIIEYFHE
FDEPAVIYSSNGNKTVWLRYAEWLLTCPVILIHLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
VYGSTVGHTIIDLMSKNCWGLLGHYLRVLIHEHILIHGDIRKTTKLNIGGTEIEVETLVEDEAEAGAVAA
*A*KSRITSEGEYIPLDQIDINVFCYENEV

Amino acid sequence of ReaChR (red shifted ChR) (SEQ ID NO:47)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS

Amino acid sequence of ReaChR (red shifted ChR) with ER export and trafficking signal sequences (SEQ ID NO:48)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVTFALSVACLGWYAYQAWRATCGWEEVYVALIEMMKSIIEAFH
EFDSPATLWLSSGNGVVWMRYGEWLLTCPVILIHLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SPYGSAIGHSILDLIAKNMWGVLGNYLRVKIHEHILLYGDIRKKQKITIAGQEMEVETLVAEEEDKYESS
*AAA*KSRITSEGEYIPLDQIDINVFCYENEV

FIG. 6 (Cont.)

Amino acid sequence of SdChR (CheRiff) (SEQ ID NO:49)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv

Amino acid sequence of SdChR (CheRiff) with ER export and trafficking signal sequences (SEQ ID NO:50)

Mggapapdahsappgndsaggseyhapagyqvnppyhpvhgyeeqcssiyiyygalweqetargfqwfavflsalfl
afygwhaykasvgweevyvcsvelikvileiyfeftspamlflyggnitpwlryaewlltcpvilihlsnitglsee
ynkrtmallvsdlgticmgvtaalatgwvkwlfyciglvygtqtfynagiiyvesyyimpaggckklvlamtavyys
swlmfpglfifgpegmhtlsvagstightiadllskniwgllghflrikihehiimygdirrpvssqflgrkvdvla
fvteedkv*AAA*KSRITSEGEYIPLDQIDINVFCYENEV

Amino acid sequence of CnChR1 (Chrimson) (SEQ ID NO:51)

Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirkttkmeiggeeveveefveeededtv

Amino acid sequence of CnChR1 (Chrimson) with ER export and trafficking signal sequences (SEQ ID NO:52)

Maelissatrslfaagginpwpnpyhhedmgcggmtptgecfstewwcdpsyglsdagygycfveatggylvvgvek
kqawlhsrgtpgekigaqvcqwiafsiaialltfygfsawkatcgweevyvccvevlfvtleifkefsspatvylst
gnhayclryfewllscpviliklsnlsglkndyskrtmglivscvgmivfgmaaglatdwlkwllyivsciyggymy
fqaakcyveanhsvpkghcrmvvklmayayfaswgsypilwavgpegllklspyansighsicdiiakefwtflahh
lrikihehilihgdirkttkmeiggeeveveefveeededtv*AAA*KSRITSEGEYIPLDQIDINVFCYENEV

Amino acid sequence of CsChrimson (SEQ ID NO:53)

Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirkttkmeiggeeveveefveeededtv

FIG. 6 (Cont.)

Amino acid sequence of CsChrimson with ER export and trafficking signal sequences (SEQ ID NO:54)

Msrlvaaswllalllcgitstttassapaasstdgtaaaavshyamngfdelakgavvpedhfvcgpadkcycsawl
hsrgtpgekigaqvcqwiafsiaialltfygfsawkatcgweevyvccvevlfvtleifkefsspatvylstgnhay
clryfewllscpviliklsnlsglkndyskrtmglivscvgmivfgmaaglatdwlkwllyivsciyggymyfqaak
cyveanhsvpkghcrmvvklmayayfaswgsypilwavgpegllklspyansighsicdiiakefwtflahhlriki
hehilihgdirkttkmeiggeeveveefveeededtv*AAA*KSRITSEGEYIPLDQIDINVFCYENEV

Amino acid sequence of ShChR1 (Chronos) (SEQ ID NO:55)

metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirktttinvag
enmeietfvdeeeeggv

Amino acid sequence of ShChR1 (Chronos) with ER export and trafficking signal sequences (SEQ ID NO:56)

metaatmthafisavpsaeatirgllsaaavvtpaadahgetsnattagadhgcfphinhgtelqhkiavglqwftv
ivaivqlifygwhsfkattgweevyvcvielvkcfielfhevdspatvyqtnggaviwlrysmwlltcpvilihlsn
ltglheeyskrtmtilvtdignivwgitaaftkgplkilffmiglfygvtcffqiakvyiesyhtlpkgvcrkicki
mayvffcswlmfpvmfiagheglglitpytsgighlildliskntwgflghhlrvkihehilihgdirktttinvag
enmeietfvdeeeeggv*AAA*KSRITSEGEYIPLDQIDINVFCYENEV

FIG. 7

(hyperpolarizing opsins)
amino acid sequence of Archaerhodopsin-3 (SEQ ID NO:57)

MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD amino acid sequence of eArch3.0 (SEQ ID NO:58)

MDPIALQAGYDLLGDGRPETLWLGIGTLLMLIGTFYFLVRGWGVTDKDAREYYAVTILVPGIASAAYLSM
FFGIGLTEVTVGGEMLDIYYARYADWLFTTPLLLLDLALLAKVDRVTIGTLVGVDALMIVTGLIGALSHT
AIARYSWWLFSTICMIVVLYFLATSLRSAAKERGPEVASTFNTLTALVLVLWTAYPILWIIGTEGAGVVG
LGIETLLFMVLDVTAKVGFGFILLRSRAILGDTEAPEPSAGADVSAAD*RPVVAAAA***KSRITSEGEYIPLD
QIDINV**FCYENEV

Amino acid sequence of ArchT (SEQ ID NO:59)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP

Amino acid sequence of ArchT with ER export and trafficking signal
sequences (SEQ ID NO:60)

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP*AAA*KSRITSEGEYIPLDQIDINVFCYENEV

FIG. 7 (Cont.)

amino acid sequence of GtR3 (SEQ ID NO:61)

MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI amino acid sequence of GtR3 with ER export and trafficking signal
sequences (SEQ ID NO:62)

MLVGEGAKLDVHGCKTVDMASSFGKALLEFVFIVFACITLLLGINAAKSKAASRVLFPATFVTGIASIAY
FSMASGGGWVIAPDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVVWVFAEGFGNFSVT
FEVLIYGVLDVISKAVFGLILMSGAATGYESI*AAA*KSRITSEGEYIPLDQIDINVFCYENEV

Amino acid sequence of rhodopsin type II proton pump (Oxy) (SEQ ID
NO:63)

MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA

Amino acid sequence of rhodopsin type II proton pump with ER export
and trafficking signal sequences (SEQ ID NO:64)

MAPLAQDWTYAEWSAVYNALSFGIAGMGSATIFFWLQLPNVTKNYRTALTITGIVTLIATYHYFRIFNSW
VAAFNVGLGVNGAYEVTVSGTPFNDAYRYVDWLLTVPLLLVELILVMKLPAKETVCLAWTLGIASAVMVA
LGYPGEIQDDLSVRWFWWACAMVPFVYVVGTLVVGLGAATAKQPEGVVDLVSAARYLTVVSWLTYPFVYI
VKNIGLAGSTATMYEQIGYSAADVTAKAVFGVLIWAIANAKSRLEEEGKLRA*AAA***KSRITSEGEYIPLDQ
IDINV**FCYENEV

FIG. 7 (Cont.)

Amino acid sequence of L. maculans rhodopsin (Mac) (SEQ ID NO:65)

MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGA

Amino acid sequence of Mac 3.0 (SEQ ID NO:66)
MIVDQFEEVLMKTSQLFPLPTATQSAQPTHVAPVPTVLPDTPIYETVGDSGSKTLWVVFVLMLIASAAFT
ALSWKIPVNRRLYHVITTIITLTAALSYFAMATGHGVALNKIVIRTQHDHVPDTYETVYRQVYYARYIDW
AITTPLLLLDLGLLAGMSGAHIFMAIVADLIMVLTGLFAAFGSEGTPQKWGWYTIACIAYIFVVWHLVLN
GGANARVKGEKLRSFFVAIGAYTLILWTAYPIVWGLADGARKIGVDGEIIAYAVLDVLAKGVFGAWLLVT
HANLRESDVELNGFWANGLNREGAIRIGEDDGARPVVAVSKAAAKSRITSEGEYIPLDQIDINV*FCYENE
V* amino acid sequence of NpHR (SEQ ID NO:67)

<u>MTETLPPVTESAVALQAEVTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD</u> amino acid sequence of NpHR3.0 (SEQ ID NO:68)

<u>MTETLPPVTESAVALQAEVTQRELFEFVLNDPLLASSLYINIALAGLSILLFVFMTRGLDDPRAKLI
AVSTILVPVVSIASYTGLASGLTISVLEMPAGHFAEGSSVMLGGEEVDGVVTMWGRYLTWALST
PMILLALGLLAGSNATKLFTAITFDIAMCVTGLAAALTTSSHLMRWFWYAISCACFLVVLYILLV
EWAQDAKAAGTADMFNTLKLLTVVMWLGYPIVWALGVEGIAVLPVGVTSWGYSFLDIVAKYI
FAFLLLNYLTSNESVVSGSILDVPSASGTPADD</u><u>AAAKSRITSEGEYIPLDQIDINFCYENEV</u> amino acid sequence of NpHR3.1 (SEQ ID NO:69)

MVTQRELFEFVLNDPLLASSLYINIALAGLSILLFVFMTRGLDDPRAKLIAVSTILVPVVSIASYTG
LASGLTISVLEMPAGHFAEGSSVMLGGEEVDGVVTMWGRYLTWALSTPMILLALGLLAGSNAT
KLFTAITFDIAMCVTGLAAALTTSSHLMRWFWYAISCACFLVVLYILLVEWAQDAKAAGTADM
FNTLKLLTVVMWLGYPIVWALGVEGIAVLPVGVTSWGYSFLDIVAKYIFAFLLLNYLTSNESVVS
GSILDVPSASGTPADD<u>AAAKSRITSEGEYIPLDQIDINFCYENEV</u>

FIG. 7 (Cont.)

**Amino acid sequence of *Dunaliella salina* channelrhodopsin** (SEQ ID NO:70)

Mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv

**Amino acid sequence of *Dunaliella salina* channelrhodopsin** with ER export and trafficking signal sequences (SEQ ID NO:71)

mrrresqlaylclfvliagwaprltesapdlaerrppserntpyanikkvpnitepnanvqldg
walyqdfyylagsdkewvvgpsdqcycrawskshgtdregeaavvwayivfaicivqlvyfmfa
awkatvgweevyvniielvhialviwvefdkpamlylndgqmvpwlrysawllscpvilihlsn
ltglkgdyskrtmgllvsdigtivfgtsaalappnhvkvilftigllyglftfftaakvyieay
htvpkgqcrnlvramawtyfvswamfpilfilgregfghityfgssighfileifsknlwsllg
hglryrirqhiiihgnltkknkiniagdnveveeyvdsndkdsdv*AAA***KSRITSEGEYIPLDQID
INV**FCYENEV

Amino acid sequence of a iC1C2 (SEQ ID NO:72)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

Amino acid sequence of a iC1C2 with ER export and trafficking signal sequences (SEQ ID NO:73)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV*AA
A*KSRITSEGEYIPLDQIDINVFCYENEV

Amino acid sequence of a SwiChR (iC1C2-C167A or T or S) (SEQ ID NO:74)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAV

FIG. 7 (Cont.)

Amino acid sequence of a SwiChR (iC1C2-C167A or T or S) with ER export and trafficking signal sequences (SEQ ID NO:75)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTXPVILIRLSNLTGLANDYNKRTMGLLVSDIGTIVWGTTAALSKG
YVRVIFFLMGLCYGIYTFFNAAKVYIEAYHTVPKGRCRQVVTGMAWLFFVSWGMFPILFILGPEGFGVLS
KYGSNVGHTIIDLMSKQCWGLLGHYLRVLIHEHILIHGDIRKTTKLNIGGTEIEVETLVEDEAEAGAVAA
AKSRITSEGEYIPLDQIDINVFCYENEV

Amino acid sequence of ibC1C2 (SEQ ID NO:76)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAV

Amino acid sequence of ibC1C2 with ER export and trafficking signal sequences (SEQ ID NO:77)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVILIRLSNLTG
LANDYNKRTMGLLVSDIGTIVWGTTAALSKGYVRVIFFLMGLCYGIYTFFNAAKVYIEAYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVAAAKSRITSEGEYIPLDQIDINVFCYENEV

Amino acid sequence of iChR2 (SEQ ID NO:78)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP

FIG. 7 (Cont.)

Amino acid sequence of iChR2 with ER export and trafficking signal sequences (SEQ ID NO:79)

MDYGGALSAVGRELLFVTNPVVVNGSVLVPEDQCYCAGWIESRGTNGAQTASNVLQWLSAGFSILLLMFY
AYQTWKSTCGWEEIYVCAISMVKVILEFFFSFKNPSMLYLATGHRVKWLRYASWLLTCPVILIRLSNLTG
LSNDYSRRTMGLLVSDIGTIVWGATSAMATGYVKVIFFCLGLCYGANTFFHAAKAYIEGYHTVPKGRCRQ
VVTGMAWLFFVSWGMFPILFILGPEGFGVLSKYGSNVGHTIIDLMSKQCWGLLGHYLRVLIHEHILIHGD
IRKTTKLNIGGTEIEVETLVEDEAEAGAVP*AAA*KSRITSEGEYIPLDQIDINVFCYENEV*

Amino acid sequence of iC1V1 (SEQ ID NO:80)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED

Amino acid sequence of iC1V1 with ER export and trafficking signal sequences (SEQ ID NO:81)

MSRRPWLLALALAVALAAGSAGASTGSDATVPVATQDGPDYVFHRAHERMLFQTSYTLENNGSVICIPNN
GQCFCLAWLKSNGTNAEKLAANILQWISFALSALCLMFYGYQTWKSTCGWEEIYVATISMIKFIIEYFHS
FDEPAVIYSSNGNKTKWLRYASWLLTCPVLLIRLSNLTGLKDDYSKRTMGLLVSDVGCIVWGATSAMCTG
WTKILFFLISLSYGMYTYFHAAKVYIEAFHTVPKGICRELVRVMAWTFFVAWGMFPVLFLLGTEGFGHIS
KYGSNIGHSILDLIAKQMWGVLGNYLRVKIHEHILLYGDIRKKQKITIAGQEMEVETLVAEEED*AAA***KSR
ITSEGEYIPLDQIDINVFCYENEV***

Amino acid sequence of ibC1V1 (SEQ ID NO:82)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEED

FIG. 7 (Cont.)

Amino acid sequence of ibC1V1 with ER export and trafficking signal sequences (SEQ ID NO:83)

MDYGGALSAVGLFQTSYTLENNGSVICIPNNGQCFCLAWLKSNGTNAEKLAANILQWISFALSALCLMFY
GYQTWKSTCGWEEIYVATISMIKFIIEYFHSFDEPAVIYSSNGNKTKWLRYASWLLTCPVLLIRLSNLTG
LKDDYSKRTMGLLVSDVGCIVWGATSAMCTGWTKILFFLISLSYGMYTYFHAAKVYIEAFHTVPKGICRE
LVRVMAWTFFVAWGMFPVLFLLGTEGFGHISKYGSNIGHSILDLIAKQMWGVLGNYLRVKIHEHILLYGD
IRKKQKITIAGQEMEVETLVAEEEDAAAKSRITSEGEYIPLDQIDINVFCYENEV

Amino acid sequence of iReaChR (SEQ ID NO:84)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS

FIG. 7 (Cont.)

Amino acid sequence of iReaChR with ER export and trafficking signal sequences (SEQ ID NO:85)

MVSRRPWLLALALAVALAAGSAGASTGSDATVPVATQDGPDYVFHRAHERMLFQTSYTLENNGSVICIPN
NGQCFCLAWLKSNGTNAEKLAANILQWVSFALSVACLGWYAYQAWRATCGWEEVYVALISMMKSIIEAFH
SFDSPATLWLSSGNGVKWMRYGSWLLTCPVILIRLSNLTGLKDDYSKRTMGLLVSDVGCIVWGATSAMCT
GWTKILFFLISLSYGMYTYFHAAKVYIEAFHTVPKGLCRQLVRAMAWLFFVSWGMFPVLFLLGPEGFGHI
SKYGSNIGHSILDLIAKQMWGVLGNYLRVKIHEHILLYGDIRKKQKITIAGQEMEVETLVAEEEDKYESS
*AAA*KSRITSEGEYIPLDQIDINVFCYENEV

Amino acid sequence of ibReaChR (SEQ ID NO:86)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS

Amino acid sequence of ibReaChR with ER export and trafficking signal sequences (SEQ ID NO:87)

MDYGGALSAVGLFQTSYTLENNGSVICIPNNGQCFCLAWLKSNGTNAEKLAANILQWVSFALSVACLGWY
AYQAWRATCGWEEVYVALISMMKSIIEAFHSFDSPATLWLSSGNGVKWMRYGSWLLTCPVILIRLSNLTG
LKDDYSKRTMGLLVSDVGCIVWGATSAMCTGWTKILFFLISLSYGMYTYFHAAKVYIEAFHTVPKGLCRQ
LVRAMAWLFFVSWGMFPVLFLLGPEGFGHISKYGSNIGHSILDLIAKQMWGVLGNYLRVKIHEHILLYGD
IRKKQKITIAGQEMEVETLVAEEEDKYESS*AAA*KSRITSEGEYIPLDQIDINVFCYENEV

CALCIUM INDICATOR POLYPEPTIDES AND METHODS OF USE THEREOF

CROSS-REFERENCE

This application claims the benefit of U.S. Provisional Patent Application No. 62/523,048, filed Jun. 21, 2017, which application is incorporated herein by reference in its entirety.

INTRODUCTION

Methods for detecting functional cellular expression are currently available, and include genetically encoded calcium indicators (GECIs) that enable long-term, repetitive and unbiased functional imaging in specific cell types in vivo. Currently, green fluorescent protein (GFP) and red fluorescent protein (RFP) based GECIs are available. The two most commonly used red GECIs are jrCaMP 1b and jrGECO 1a, which have high basal activity and slow kinetics. Additional disadvantages of currently available red GECIs include accumulation in lysosomes with long-term expression, and lack of functional signal production.

There is a need in the art for improved calcium indicators.

SUMMARY

The present disclosure provides a genetically encoded calcium indicator (GECI), nucleic acids encoding the GECI, and host cells comprising the GECI. The present disclosure also provides methods of detecting a change in the intracellular concentration of a cell expressing a GECI of the present disclosure.

BRIEF DESCRIPTION OF THE DRAWINGS

FIG. 1 provides the amino acid sequence of the GECI (SEQ ID NO:1).

FIG. 2 provides the amino acid sequence of the jRGECO 1a (SEQ ID NO:2).

FIG. 6 provides amino acid sequences of depolarizing opsins.

FIG. 7 provides amino acid sequences of hyperpolarizing opsins.

DEFINITIONS

Figure 3:
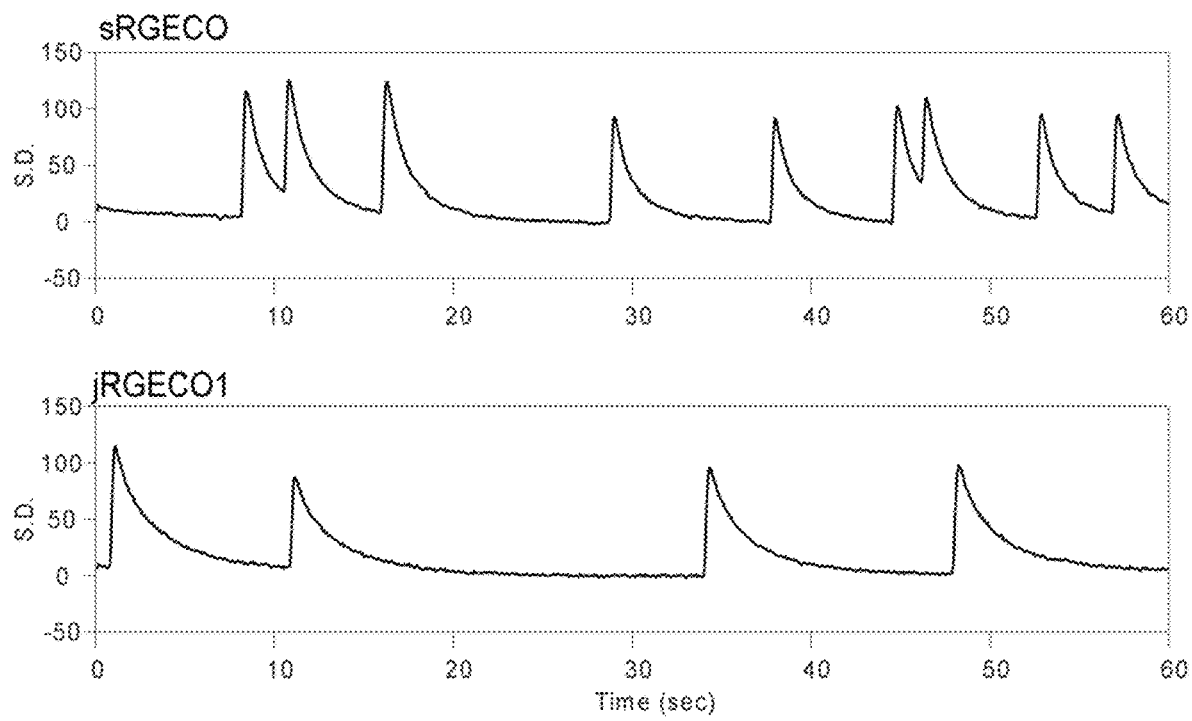
FIG. 3 shows a comparison of the excitation trace of jRGECO1-E217D (GECI with a substitution of Glu-217 to 217D) to jrGECO.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

An "isolated" polypeptide or an "isolated" nucleic acid is one that has been identified and separated and/or recovered from a component of its natural environment. Contaminant components of its natural environment are materials that would interfere with use of the polypeptide or nucleic acid, and may include enzymes, hormones, and other proteinaceous or nonproteinaceous solutes. In some embodiments, the polypeptide or nucleic acid will be purified to greater than 80%, greater than 85%, greater than 90%, greater than 95%, or greater than 98%, by weight.

The term "genetic modification" refers to a permanent or transient genetic change induced in a cell following introduction into the cell of a heterologous nucleic acid (e.g., a nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, use of a CRISPR/Cas9 system, and the like.

A "host cell," as used herein, denotes an in vivo or in vitro eukaryotic cell, or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a GECI of the present disclosure; an expression vector that comprises a nucleotide sequence encoding a component of a GECI of the present disclosure; or any other nucleic acid or expression vector described herein), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell, where such nucleic acids and expression vectors are described herein.

"Operably linked" refers to a juxtaposition wherein the components so described are in a relationship permitting them to function in their intended manner. For instance, a promoter is operably linked to a coding region of a nucleic acid if the promoter affects transcription or expression of the coding region of a nucleic acid.

A "vector" or "expression vector" is a replicon, such as plasmid, phage, virus, or cosmid, to which another DNA segment, i.e. an "insert", may be attached so as to bring about the replication of the attached segment in a cell.

"Heterologous," as used herein, refers to a nucleotide or polypeptide sequence that is not found in the native (e.g., naturally-occurring) nucleic acid or protein, respectively.

As used herein, the term "affinity" refers to the equilibrium constant for the reversible binding of two agents (e.g., a protease and a polypeptide comprising a protease cleavage site) and is expressed as Km. Km is the concentration of peptide at which the catalytic rate of proteolytic cleavage is half of Vmax (maximal catalytic rate). Km is often used in the literature as an approximation of affinity when speaking about enzyme-substrate interactions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a genetically encoded calcium indicator (GECI) and nucleic acids encoding same. The present disclosure also provides methods of monitoring the activity of a cell, the method comprising stimulating a cell comprising the GECI of the present disclosure and detecting fluorescence emitted by the cell.

Calcium Indicator (GECI) Polypeptides

The present disclosure provides a calcium indicator polypeptide, also referred to herein as a "genetically encoded calcium indicator" or "GECI."

In some cases, a calcium indicator polypeptide of the present disclosure comprises: a) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVH-MEGSVNGHEFEIEGEGEGRPYEAFQTAKLKVTKGG-PLPFAWDILSPQFMY GSKAYIKHPAD-IPDYFKLSFPEGF RWDRVMNFEDGGIIHVNQDSSLQDGVFIYKVKLRG TNFPPDGPVMQKKTMGWEATR (SEQ ID NO:3), where amino acid 86 is an aspartic acid; and b) a calcium-binding polypeptide. In some cases, the calcium-binding polypeptide is a calmodulin polypeptide. In some cases, the calcium-binding polypeptide is a troponin C polypeptide.

In some cases, a calcium indicator polypeptide of the present disclosure comprises: a) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVH-MEGSVNGHEFEIEGEGEGRPYEAFQTAKLKVTKGG-PLPFAWDILSPQFMY GSKAYIKHPAD-IPDYFKLSFPEGF RWDRVMNFEDGGIIHVNQDSSLQDGVFIYKVKLRG TNFPPDGPVMQKKTMGWEATR (SEQ ID NO:4), where amino acid 86 is aspartic acid; b) a calcium-binding polypeptide; and c) a calmodulin-binding polypeptide.

In some cases, a calcium indicator polypeptide of the present disclosure comprises, in order from N-terminus to C-terminus: a) a calmodulin-binding polypeptide; b) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVHMEGSVNGHEFEIEGEGEGRP-YEAFQTAKLKVTKGGPLPFAWDILSPQFMY GSKAY-IKHPADIPDYFKLSFPEGF RWDRVMNFEDGGIIHVNQDSSLQDGVFIYKVKLRG TNFPPDGPVMQKKTMGWEATR (SEQ ID NO:5), where amino acid 86 is Asp; and c) a calmodulin polypeptide. In some cases, a calcium indicator polypeptide of the present disclosure comprises, in order from N-terminus to C-terminus: a) a calmodulin-binding polypeptide; b) a calmodulin-binding polypeptide; and c) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVH-MEGSVNGHEFEIEGEGEGRPYEAFQTAKLKVTKGG-PLPFAWDILSPQFMY GSKAYIKHPAD-IPDYFKLSFPEGF RWDRVMNFEDGGIIHVNQDSSLQDGVFIYKVKLRG TNFPPDGPVMQKKTMGWEATR (SEQ ID NO:6), where amino acid 86 is Asp.

In some cases, a calcium indicator polypeptide of the present disclosure comprises: a) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVH-MEGSVNGHEFEIEGEGEGRPYEAFQTAKLKVTKGG-PLPFAWDILSPQFMY GSKAYIKHPAD-IPDYFKLSFPEGF RQDRVMNFEDGGIIHVNQDSSLQDGVFIYKVKLRG TNFPPDGPVMQKKTMGWEATR (SEQ ID NO:7), where amino acid 85 is glutamine, and where amino acid 86 is an aspartic acid; and b) a calcium-binding polypeptide. In some cases, the calcium-binding polypeptide is a calmodulin polypeptide. In some cases, the calcium-binding polypeptide is a troponin C polypeptide.

In some cases, a calcium indicator polypeptide of the present disclosure comprises: a) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVH-MEGSVNGHEFEIEGEGEGRPYEAFQTAKLKVTKGG-PLPFAWDILSPQFMY GSKAYIKHPAD-IPDYFKLSFPEGF RQDRVMNFEDGGIIHVNQDSSLQDGVFIYKVKLRG TNFPPDGPVMQKKTMGWEATR (SEQ ID NO:8), where amino acid 85 is glutamine, and where amino acid 86 is aspartic acid; b) a calcium-binding polypeptide; and c) a calmodulin-binding polypeptide.

In some cases, a calcium indicator polypeptide of the present disclosure comprises, in order from N-terminus to C-terminus: a) a calmodulin-binding polypeptide; b) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVHMEGSVNGHEFEIEGEGEGRP-YEAFQTAKLKVTKGGPLPFAWDILSPQFMY GSKAY-IKHPADIPDYFKLSFPEGF RQDRVMNFEDGGIIHVNQDSSLQDGVFIYKVKLRG TNFPPDGPVMQKKTMGWEATR (SEQ ID NO:9), where amino acid 85 is glutamine, and where amino acid 86 is Asp; and c) a calmodulin polypeptide. In some cases, a calcium indicator polypeptide of the present disclosure comprises, in order from N-terminus to C-terminus: a) a calmodulin-binding polypeptide; b) a calmodulin-binding polypeptide; and c) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVHMEGSVNGHE-FEIEGEGEGRPYEAFQTAKLKVTKGGPLPFAWDIL-SPQFMY GSKAYIKHPADIPDYFKLSFPEGF RQDRVMNFEDGGIIHVNQDSSLQDGVFIYKVKLRG TNFPPDGPVMQKKTMGWEATR (SEQ ID NO:10), where amino acid 85 is glutamine, and where amino acid 86 is Asp.

Calmodulin Polypeptides

Suitable calmodulin polypeptides include a calcium-binding polypeptide having a length of from about 145 amino acids to about 150 amino acids, and comprising an amino acid sequence having at least 80%, at least 85%, at least 90%, at least 95%, at least 98%, at least 99%, or 100%, amino acid sequence identity to the following amino acid sequence:

```
                                         (SEQ ID NO: 11)
DDLTEEQIAEFKEAFSLFDKDGDGTITTKELGTVFRSLGQNPTEAELQDM

INEVDADGDGTFDFPEFLTMMARKMNDTDSEEEIREAFRVFDKDGNGYIG

AAELRHVMTDLGEKLTDEEVDEMIRVADIDGDGQVNYEEFVQMMTAK.
```

In some cases, the calmodulin polypeptide comprises an Asp→Gln substitution at an amino acid corresponding to D2. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DQLTEEQI-AEFKEAFSLFDKDGDGTITTKELGTVFRSLGQNPTE-AELQDMINEVDADGD GTFDFPEFLTM-MARKMNDTDSEEEIREAFRVFDKDGNGYIGAA-ELRHVMTDLGEKLTDE EVDEMIRVADIDGDGQVNY-EEFVQMMTAK (SEQ ID NO:12), where amino acid 2 is Gln.

In some cases, the calmodulin polypeptide comprises a Phe→Met substitution at a position corresponding to amino acid 35. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DDLTEEQI-AEFKEAFSLFDKDGDGTITTKELGTVMRSLGQNPTE-AELQDMINEVDADGD GTFDFPEFLTM-MARKMNDTDSEEEIREAFRVFDKDGNGYIGAAE-LRHVMTDLGEKLTDE EVDEMIRVADIDGDGQVNY-EEFVQMMTAK (SEQ ID NO:13), where amino acid 35 is Met.

In some cases, the calmodulin polypeptide comprises an Asp→Gln substitution at an amino acid corresponding to D2 and a Phe→Met substitution at a position corresponding to amino acid 35. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DQLTEEQIAEFKEAFSLFDKDGDGTITTKEL-GTVMRSLGQNPTEAELQDMINEVDADGD GTFDFPE-FLTMMARKMNDTDSEEEIREAFRVFDKDGNGYI-GAAELRHVMTDLGEKLTDE EVDEMIRVADIDGDGQVNYEEFVQMMTAK (SEQ ID NO:14), where amino acid 2 is Gln, and where amino acid 35 is Met.

In some cases, the calmodulin polypeptide comprises a Phe→Leu substitution at a position corresponding to amino acid 35. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DDLTEEQI-AEFKEAFSLFDKDGDGTITTKELGTVLRSLGQNPTE-AELQDMINEVDADGD GTFDFPEFLTM-MARKMNDTDSEEEIREAFRVFDKDGNGYIGAA-ELRHVMTDLGEKLTDE EVDEMIRVADIDGDGQVNY-EEFVQMMTAK (SEQ ID NO:15), where amino acid 35 is Leu.

In some cases, the calmodulin polypeptide comprises an Asp→Gln substitution at an amino acid corresponding to D2 and a Phe→Leu substitution at a position corresponding to amino acid 35. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DQLTEEQIAEFKEAFSLFDKDGDGTITTKEL-GTVLRSLGQNPTEAELQDMINEVDADGD GTFDFPE-FLTMMARKMNDTDSEEEIREAFRVFDKDGNGYI-GAAELRHVMTDLGEKLTDE EVDEMIRVADIDGDGQVNYEEFVQMMTAK (SEQ ID NO:16), where amino acid 2 is Gln, and where amino acid 35 is Leu.

In some cases, the calmodulin polypeptide comprises an Ile→Met substitution at amino acid 26. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DDLTEEQI-AEFKEAFSLFDKDGDGTMTTKELGTVFRSLGQNPTE-AELQDMINEVDADGD GTFDFPEFLTM-MARKMNDTDSEEEIREAFRVFDKDGNGYIGAAE-LRHVMTDLGEKLTDE EVDEMIRVADIDGDGQVNY-EEFVQMMTAK (SEQ ID NO:17), where amino acid 26 is Met.

In some cases, the calmodulin polypeptide comprises a Leu→Ile substitution at amino acid 121. Thus, in some cases, a suitable calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence: DDLTEEQI-AEFKEAFSLFDKDGDGTITTKELGTVFRSLGQNPTE-AELQDMINEVDADGD GTFDFPEFLTMMARKMNDTDSEEEIRE-AFRVFDKDGNGYIGAAELRHVMTDLGEKITDE EVDEMIRVADIDGDGQVNYEEFVQMMTAK (SEQ ID NO:18), where amino acid 121 is Ile.

Calmodulin-Binding Polypeptides

Suitable calmodulin-binding polypeptides include a calmodulin-binding polypeptide having a length of from 130 amino acids to 135 amino acids and comprising an amino acid sequence having at least 80%, at least 85%, at least 90%, at least 95%, at least 98%, at least 99%, or 100%, amino acid sequence identity to the following amino acid sequence:

```
                                    (SEQ ID NO: 19)
MVDSSRRKWNKAGHAVRAIGRLSSPVVSERMYPEDGALKSEIKKGLRLKD

GGHYAAEVKTTYKAKKPVQLPGAYIVDIKLDIVSHNEDYTIVEQCERAEG

RHSTGGMDELYKGGTGGSLVSKGEEDNMAII.
```

Troponin C Polypeptides and Troponin I Polypeptides

A suitable troponin C polypeptide comprises an amino acid sequence having at least 80%, at least 85%, at least 90%, at least 95%, at least 98%, at least 99%, or 100%, amino acid sequence identity to the following troponin C amino acid sequence:

```
                                    (SEQ ID NO: 20)
MTDQQAEARS YLSEEMIAEF KAAFDMFDAD GGGDISVKEL

GTVMRMLGQT PTKEELDAII EEVDEDGSGT IDFEEFLVMM

VRQMKEDAKG KSEEELAECF RIFDRNADGY IDPGELAEIF

RASGEHVTDE EIESLMKDGD KNNDGRIDFD EFLKMMEGVQ.
```

A suitable troponin C polypeptide can have a length of from about 100 amino acids to about 175 amino acids, e.g., from about 100 amino acids to about 125 amino acids, from about 125 amino acids to about 150 amino acids, or from about 150 amino acids to about 175 amino acids.

A suitable troponin C polypeptide comprises an amino acid sequence having at least 80%, at least 85%, at least 90%, at least 95%, at least 98%, at least 99%, or 100%, amino acid sequence identity to the following troponin C amino acid sequence: MTDQQAEARSYLSEEMIAEF-KAAFDMFDADGGGDISVKELGTVMRMLGQTPT KEELDAIIEEVDEDGSGTIDFEEFLVMMVRQMKE-DAKGKSEEELAECFRIFDRDA NGYIDAEELAEI-FRASGEHVTDEEIESLMKDGDKNNDGRIDFDE-FLKMMEGVQ (SEQ ID NO:21); and has a length of from about 160 amino acids to about 175 amino acids (e.g., from about 160 amino acids to about 165 amino acids, from about 165 amino acids to about 170 amino acids, or from about 170 amino acids to about 175 amino acids. In some cases, a suitable troponin C polypeptide comprises the amino acid sequence: MTDQQAEARSYLSEEMIAEFKAAFDMF-DADGGGDISVKELGTVMRMLGQTPT KEEL-DAIIEEVDEDGSGTIDFEEFLVMMVRQMKEDAKGK-SEEELAECFRIFDRDA NGYIDAEELAEIFRASGEHVTDEE-IESLMKDGDKNNDGRIDFDEFLKMMEGVQ (SEQ ID NO:22); and has a length of 160 amino acids.

Where a calcium indicator polypeptide of the present disclosure comprises a troponin C polypeptide, in some cases, the calcium indicator polypeptide further includes a troponin I polypeptide.

In some cases, a suitable troponin I polypeptide comprises an amino acid sequence having at least 80%, at least 85%, at least 90%, at least 95%, at least 98%, at least 99%, or 100%, amino acid sequence identity to the following troponin I amino acid sequence:

```
                                          (SEQ ID NO: 23)
MPEVERKPKI  TASRKLLLKS  LMLAKAKECW  EQEHEEREAE

KVRYLAERIP  TLQTRGLSLS  ALQDLCRELH  AKVEVVDEER

YDIEAKCLHN  TREIKDLKLK  VMDLRGKFKR  PPLRRVRVSA

DAMLRALLGS  KHKVSMDLRA  NLKSVKKEDT  EKERPVEVGD

WRKNVEAMSG  MEGRKKMFDA  AKSPTSQ.
```

A fragment of troponin I can be used. See, e.g., Tung et al. (2000) *Protein Sci.* 9:1312. For example, troponin I (95-114) can be used. Thus, for example, in some cases, the troponin I polypeptide can comprise an amino acid sequence having at least 80%, at least 85%, at least 90%, at least 95%, at least 98%, at least 99%, or 100%, amino acid sequence identity to the following troponin I amino acid sequence: KDLKLK VMDLRGKFKR PPLR (SEQ ID NO:24); and has a length of about 20 amino acids to about 50 amino acids (e.g., from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids). In some cases, the troponin I polypeptide has a length of 20 amino acids. In some cases, the troponin I polypeptide has the amino acid sequence: KDLKLK VMDLRGKFKR PPLR (SEQ ID NO:24); and has a length of 20 amino acids.

In some cases, a suitable troponin I polypeptide comprises an amino acid sequence having at least 80%, at least 85%, at least 90%, at least 95%, at least 98%, at least 99%, or 100%, amino acid sequence identity to the following troponin I amino acid sequence: RMSADAMLKALLGSKHK-VAMDLRAN (SEQ ID NO:25); and has a length of from about 25 amino acids to about 50 amino acids (e.g., from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids). In some cases, the troponin I polypeptide has the amino acid sequence: RMSADAML-KALLGSKHKVAMDLRAN (SEQ ID NO:25); and has a length of 25 amino acids.

In some cases, a suitable troponin I polypeptide comprises an amino acid sequence having at least 80%, at least 85%, at least 90%, at least 95%, at least 98%, at least 99%, or 100%, amino acid sequence identity to the following troponin I amino acid sequence: NQKLFDLRGKFKRP-PLRRVRMSADAMLKALLGSKHKVAMDLRAN (SEQ ID NO:26); and has a length of from about 44 amino acids to about 50 amino acids (e.g., 44, 45, 46, 47, 4, 49, or 50 amino acids). In some cases, the troponin I polypeptide has the amino acid sequence: NQKLFDLRGKFKRP-PLRRVRMSADAMLKALLGSKHKVAMDLRAN (SEQ ID NO:26); and has a length of 44 amino acids.

Exemplary Calcium Indicator Polypeptides

In some cases, a GECI of the present disclosure comprises an amino acid sequence having at least 80%, at least 85%, at least 90%, at least 95%, at least 98%, at least 99%, or 100%, amino acid sequence identity to the amino acid sequence set forth in SEQ ID NO:1, where the GECI comprises a substitution of Glu-217 based on the amino acid numbering of SEQ ID NO:1. A GECI of the present disclosure has an amino acid length from about 415 amino acids to about 440 amino acids, e.g., from about 415 amino acids to about 417 amino acids, from about 417 amino acids to about 420 amino acids, from about 420 amino acids to about 425 amino acids, from about 425 amino acids to about 430 amino acids, or from about 430 amino acids to about 440 amino acids. In some cases, a GECI of the present disclosure has a length of 417 amino acids.

In some cases, the Glu-217 is substituted with aspartic acid at a position corresponding to D217 in SEQ ID NO:1). In some cases, the GECI further comprises a substitution of Glu-267 (where the amino acid numbering is according to SEQ ID NO:1). In such cases, the Glu-267 is substituted with aspartic acid at position 265 (265D). In some cases, the GECI further comprises a substitution of Trp-216 (where the amino acid numbering is according to SEQ ID NO:1). In such cases, the Trp-216 is substituted with glutamine at position 216 (216Q). In some cases, the substitutions of Glu-217, Glu-267, and Trp-216 are substituted individually. In some cases, each of Glu-217, Glu-267, and Trp-216 are substituted.

In some cases, a GECI of the present disclosure comprises an amino acid sequence having at least 80%, at least 85%, at least 90%, at least 95%, at least 98%, at least 99%, or 100%, amino acid sequence identity to the amino acid sequence set forth in SEQ ID NO:1, where amino acid 217 is Asp. In some cases, a GECI of the present disclosure comprises an amino acid sequence having at least 80%, at least 85%, at least 90%, at least 95%, at least 98%, at least 99%, or 100%, amino acid sequence identity to the amino acid sequence set forth in SEQ ID NO:1, where amino acid 216 is Gln and amino acid 217 is Asp. In some cases, a GECI of the present disclosure comprises an amino acid sequence having at least 80%, at least 85%, at least 90%, at least 95%, at least 98%, at least 99%, or 100%, amino acid sequence identity to the amino acid sequence set forth in SEQ ID NO:1, where amino acid 216 is Gln, amino acid 217 is Asp, and amino acid 267 is Asp.

Additional Sequences

A calcium indicator polypeptide of the present disclosure can include one or more additional polypeptides. Suitable additional polypeptides include, e.g., subcellular localization peptides; epitope tags; polypeptides that provide for ease of purification; and the like. In some cases, the subcellular localization peptide is a nuclear localization sequence (NLS).

Functional Features

A calcium indicator polypeptide of the present disclosure exhibits one or more of: i) low basal activity; ii) improved signal to noise ratio; iii) faster kinetics; iv) improved intracellular trafficking; v) reduced formation of aggregates; and vi) reduced localization to lysosomes, compared to a calcium indicator polypeptide comprising the amino acid sequence depicted in FIG. 2 and set forth in SEQ ID NO:2.

In some cases, a calcium indicator polypeptide of the present disclosure displays basal activity that is at least 5%, at least 10%, at least 15%, at least 20%, at least 25%, at least 30%, at least 35%, at least 40%, at least 45%, at least 50%, at least 55%, at least 60%, at least 70%, or at least 80% lower than the basal activity displayed by a calcium indicator polypeptide comprising the amino acid sequence depicted in FIG. 2 and set forth in SEQ ID NO:2.

In some cases, a calcium indicator polypeptide of the present disclosure exhibits a signal-to-noise ratio that is at least 10%, at least 20%, at least 25%, at least 50%, at least 2-fold, at least 2.5-fold, at least 3-fold, at least 4-fold, or at least 5-fold, higher than the signal-to-noise ratio exhibited by a calcium indicator polypeptide comprising the amino acid sequence depicted in FIG. 2 and set forth in SEQ ID NO:2. In some cases, a calcium indicator polypeptide of the present disclosure exhibits a signal-to-noise ratio of at least 2:1, at least 5:1, at least 10:1, at least 25:1, at least 50:1, at least 100:1, at least 200:1, at least 300:1, at least 400:1, or at least 500:1. In some cases, a calcium indicator polypeptide of the present disclosure exhibits a signal-to-noise ratio of from about 10:1 to about 25:1, from about 25:1 to about 50:1, from about 50:1 to about 100:1, from about 100:1 to about 500:1, or more than 500:1.

In some cases, a calcium indicator polypeptide of the present disclosure exhibits kinetics that are at least 10%, at least 20%, at least 25%, at least 50%, at least 2-fold, at least 2.5-fold, at least 3-fold, at least 4-fold, at least 5-fold, at least 10-fold, at least 20-fold, at least 50-fold, or at least 100-fold, faster than the kinetics displayed by a calcium indicator polypeptide comprising the amino acid sequence depicted in FIG. 2 and set forth in SEQ ID NO:2.

In some cases, a calcium indicator polypeptide of the present disclosure exhibits reduced formation of aggregates, compared to a calcium indicator polypeptide comprising the amino acid sequence depicted in FIG. 2 and set forth in SEQ ID NO:2. For example, in some cases, a calcium indicator polypeptide of the present disclosure exhibits at least 5%, at least 10%, at least 15%, at least 20%, at least 25%, at least 30%, at least 35%, at least 40%, at least 45%, at least 50%, at least 55%, at least 60%, at least 70%, or at least 80%, less aggregate formation than a calcium indicator polypeptide comprising the amino acid sequence depicted in FIG. 2 and set forth in SEQ ID NO:2.

In some cases, a calcium indicator polypeptide of the present disclosure exhibits reduced localization to lysosomes, compared to a calcium indicator polypeptide comprising the amino acid sequence depicted in FIG. 2 and set forth in SEQ ID NO:2. For example, in some cases, a calcium indicator polypeptide of the present disclosure exhibits at least 5%, at least 10%, at least 15%, at least 20%, at least 25%, at least 30%, at least 35%, at least 40%, at least 45%, at least 50%, at least 55%, at least 60%, at least 70%, or at least 80%, reduced localization to lysosomes, compared to a calcium indicator polypeptide comprising the amino acid sequence depicted in FIG. 2 and set forth in SEQ ID NO:2.

Nucleic Acids, Expression Vectors, and Host Cells

Nucleic acids comprising a nucleotide sequence that encodes a calcium indicator polypeptide of the present disclosure are provided herein. In some cases, the nucleic acid is present within an expression vector; thus, the present disclosure provides a recombinant expression vector that comprises a nucleotide sequence that encodes a calcium indicator polypeptide of the present disclosure.

In some cases, a nucleotide sequence encoding a calcium indicator polypeptide of the present disclosure is operably linked to a transcriptional control element such as a promoter. In some cases, a nucleotide sequence encoding a calcium indicator polypeptide of the present disclosure is operably linked to a promoter. In some cases, the promoter is a constitutive promoter. In some cases, the promoter is a regulatable promoter. For example, in some cases, the promoter is an inducible promoter or a repressible promoter. In some cases, the promoter is a cell type-specific promoter or a tissue-specific promoter.

Any suitable promoter that functions in a target cell can be used for expression of a calcium indicator polypeptide of the present disclosure. In certain embodiments, a promoter sequence can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

In some cases, the promoter is a neuron-specific promoter. Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. No. 6,649,811, U.S. Pat. No. 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of $Ca^{2+}$-calmodulin-dependent protein kinase II (CaMKIIα) promoter (see, e.g., Mayford et al. (1996) Proc. Natl. Acad. Sci. USA 93:13250).

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some cases, a nucleic acid encoding the GECI of the present disclosure is a recombinant expression vector. In some cases, the recombinant expression vector is a viral construct, e.g., a recombinant adeno-associated virus (AAV) construct, a recombinant adenoviral construct, a recombinant lentiviral construct, a recombinant retroviral vector, etc. In some cases, a nucleic acid of the present disclosure is a recombinant lentivirus vector. In some cases, a nucleic acid of the present disclosure is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some cases, a nucleic acid of the present disclosure is packaged in a viral particle. For example, in some cases, the nucleic acid comprising a nucleotide sequence encoding the GECI of the present disclosure is a recombinant AAV vector, and is packaged in recombinant AAV particles. Thus, in some cases, the present disclosure provides a recombinant viral particle comprising a nucleic acid of the present disclosure.

Vectors typically contain an origin of replication and one or more regulatory regions. Regulatory regions include, but are not limited to, promoters, enhancers, inducible elements, protein binding sequences, 5' or 3' untranslated regions (UTRs), transcriptional start sites, termination sequences, and poly-adenylation sequences.

In some cases, the regulatory region is a promoter. Promoters may be obtained from various sources including, for example, viruses such as polyoma, Simian Virus 40 (SV40), adenovirus, retroviruses, hepatitis B virus, and cytomegalovirus (CMV), or promoters from mammalian cells, e.g. beta-actin promoter or EF1-alpha promoter. In addition, promoters native to the host cell also are useful herein.

Additional vectors and promoters can be found in, for example, U.S. Pat. No. 9,488,642, the disclosure of which is hereby incorporated by reference in its entirety.

Genetically Modified Host Cell

Aspects of the present disclosure include a genetically modified host cell genetically modified with the nucleic acid comprising a nucleotide sequence encoding a GECI of the present disclosure. Cells comprising the GECIs, the GECI-encoding nucleic acids, or vectors comprising the GECI-encoding nucleic acids are provided.

The present disclosure provides isolated genetically modified host cells (e.g., in vitro cells) that are genetically modified with a subject nucleic acid or a subject recombinant expression vector. In some cases, a subject isolated genetically modified host cell can produce a calcium indicator polypeptide of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. In some cases, the mammalian cell is a neuron, e.g., a non-immortalized (primary) neuron. In other cases, the mammalian cell is an immortalized cell line. In some cases, the mammalian cell is a cardiac cell. In some cases, the mammalian cell is a stem cell.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some cases, the cell can be, for example, a eukaryotic or prokaryotic cell. Suitable cells include, but are not limited to cells of *Eschericia coli, Pseudomonas, Bacillus, Streptomyces*; fungi cells such as yeasts (*Saccharomyces*, and yeast such as *Pichia, Candida, Hansenula,* and *Torulopsis*); and animal cells, such as CHO, R1.1, B-W and LM cells, African Green Monkey kidney cells (for example, COS 1, COS 7, BSC1, BSC40, and BMT10), and insect cells (for example, Sf9). Suitable cells also include, but are not limited to, human cells. Representative human cells include, for example, HeLa cells or human embryonic kidney (HEK) cells.

In some cases, the cell is a brain cell. In some cases, the cell is a motor neuron, a trigeminal neuron, or an ASH neuron. In some cases, the motor neuron includes terminals in the neuro-muscular junction (NW). In some cases, the cell is a neuronal cell, a muscle cell, or a cardiomyocyte. In some cases, the cells that can be used herein are commercially available from, for example, the American Type Culture Collection (ATCC; PO Box 1549, Manassas, Va. 20108). See also Ausubel et al., 1998, Current Protocols in Molecular Biology, John Wiley & Sons, New York, N.Y.

In some cases, the GECI-encoding nucleic acid is integrated into the genome of the host cell. In some cases, the GECI-encoding nucleic acid is not integrated into the genome of the host cell and instead remains extrachromosomal.

Methods of introducing nucleic acids into cells are known and the method of transformation and choice of expression vector will depend on the host system selected. Transformation and transfection methods are described, e.g., in Ausubel et al. (1998, Current Protocols in Molecular Biology, John Wiley & Sons, New York, N.Y., (1998)), and, as described above, expression vectors may be chosen from examples known in the art. There are a number of compositions and methods which can be used to deliver the nucleic acid molecules and subsequently encoded polypeptides to cells, either in vitro or in vivo. These methods and compositions can largely be broken down into two classes: viral-based delivery systems and non-viral-based delivery systems. Such delivery systems are well known in the art and are readily adaptable for use with the compositions and methods described herein.

Also provided are transgenic animals that include a GECI-encoding nucleic acid described herein. "Animal" refers to non-human animals, including, mammals, amphibians and birds. Non-limiting examples include sheep, feline, bovines, ovines, pigs, horses, rabbits, guinea pigs, mice, hamsters, rats, non-human primates, and the like. As used herein, transgenic animal refers to any animal in which one or more of the cells of the animal contain a heterologous nucleic acid. Methods for making transgenic animals have been described, for example, in Wagner et al. (1981, PNAS USA, 78:5016-5020); Stewart et al. (1982, Science, 217: 1046-1048); Constantini et al. (1981, Nature, 294:92-94); Lacy et al. (1983, Cell, 34:343-358); McKnight et al. (1983, Cell, 34:335-341); Brinstar et al. (1983, Nature, 306:332-336); Palmiter et al. (1982, Nature, 300:611-615); Palmiter et al. (1982, Cell, 29:701-710); and Palmiter et al. (1983, Science, 222:809-814). Methods for making transgenic animals also are described in U.S. Pat. Nos. 6,175,057; 6,180, 849; and 6,133,502.

One or more of the nucleic acid sequences, polypeptides, vectors or cells described herein, or combinations thereof, can be packaged into an article of manufacture (i.e., a kit) using containers, vials, or the like.

Methods

A calcium indicator polypeptide of the present disclosure is useful for detecting changes in the intracellular calcium concentration of a cell. For example, the intracellular calcium concentration of a cell can change in response to a stimulus. Thus, the present disclosure provides methods of detecting a change in the intracellular calcium concentration of a cell; and methods of detecting a response of a cell to a stimulus, where the stimulus results in a change in the intracellular calcium concentration of the cell. A calcium indicator polypeptide of the present disclosure can be used to detect a change in the intracellular calcium concentration of a cell over time, e.g., at a first time point and at a second time point, where the second time point is later than the first time point.

The present disclosure provides a method of imaging calcium in a eukaryotic cell or tissue, where the cell or the tissue (e.g., cells in the tissue) express a GECI of the present disclosure; the method generally involves detecting fluorescence emitted by the GECI. In some cases, the cell is a neuron. In some cases, the tissue is brain tissue. In some cases, the cell is a cell of the neocortex, the hippocampus, the cerebellum, olfactory bulb, or other brain region. In some cases, the imaging is carried out over time; e.g., an image is generated at a first time point and an image it generated at a second time point, where the second time point is later than the first time point. The images can be compared to determine the effect of a stimulus (e.g., a small molecule; a polypeptide; a nucleic acid; light; heat; contact with another cell; etc.) on the calcium levels inside the cell.

The present disclosure provides methods of monitoring the activity of a cell, the method comprising stimulating a cell comprising a GECI of the present disclosure; and detecting fluorescence emitted by the cell.

A method of measuring an action potential in a cell and a method of imaging a calcium ion in a cell, which use the calcium indicator protein according to the present disclosure, can be applied to the identification of an agent that affects the cellular action potential and the intracellular calcium ion concentration. For example, animals to which a test substance has been administered or cells treated with a test substance at the individual level, tissue level, or cellular level are used, and cellular action potentials or the like in the cells are recorded. The recorded cellular action potentials are then compared with cellular action potentials or the like acquired in the same manner without treatment with the test substance. Then, it is determined whether or not the test substances affect the cellular action potentials or the like. Then, substances that function to increase or suppress the cellular action potentials or the like are selected. The test substances may be various synthetic or natural compounds, peptides, proteins, and nucleic acids such as DNA and RNA, for example. When a nucleic acid is used, the gene encoded by the nucleic acid is expressed in cells by transfection, and then the change of the cellular action potentials or the like are recorded.

The present disclosure provides methods of detecting a response of a cell to a stimulus, where the cell expresses a GECI of the present disclosure. In some cases, the stimulus is a ligand, where the cell is contacted with the ligand. In some cases, the stimulus is an electrical stimulus. In some cases, an electrical stimulus can be delivered, for example, from an extracellular electrode, or from an intracellular electrode, a magnetic resonance imaging (MRI) device, or any other type of electrical stimulus. Such electrical stimulations are well known in the art and are readily adaptable for use with the compositions and methods described herein. In some cases, the stimulus is contact with a second cell, e.g., the stimulus is cell-cell interaction. In some cases, the stimulus is heat. In some cases, the stimulus is a change in temperature, e.g., an increase in temperature or a decrease in temperature.

Optogenetics

In some cases, stimulating the cell comprises activating the cell with light, wherein the cell expresses a light-activated polypeptide. In some cases, the light-activated polypeptide is a hyperpolarizing opsin. In some cases, the light-activated polypeptide is a depolarizing opsin.

In some cases, the genetically modified host cell is genetically modified with the nucleic acid comprising a nucleotide sequence encoding a GECI of the present disclosure and a nucleic acid comprising a nucleotide sequence encoding a light-activated polypeptide.

Any microbial opsin that can be used to promote neural cell membrane hyperpolarization or depolarization in response to light may be used. For example, the Halorhodopsin family of light-responsive chloride pumps (e.g., NpHR, NpHR2.0, NpHR3.0, NpHR3.1) and the GtR3 proton pump can be used to promote neural cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

Additionally, members of the Channelrhodopsin family of light-responsive cation channel proteins (e.g., ChR2, SFOs, SSFOs, C1V1s) can be used to promote neural cell membrane depolarization or depolarization-induced synaptic depletion in response to a light stimulus. The Channelrhodopsin family of light-responsive cation channel proteins is well known in the art; see for example, WO2014144409, the disclosure of which is hereby incorporated by reference in its entirety.

Light-Activated Polypeptides

Aspects of the present disclosure include stimulating a cell by activating the cell with light, wherein the cell expresses a light-activated polypeptide and a calcium indicator polypeptide of the present disclosure. In some cases, the cell is a brain cell. In some cases, the cell is in a biological sample from a subject. In some cases, the subject is a human or a non-human animal. In some cases, said stimulating step is performed in vivo.

In some cases, the light-activated polypeptide is a light-activated ion channel or a light-activated ion pump. In some embodiments, the light-activated polypeptide depolarizes the neuron when activated by light of an activating wavelength. Suitable depolarizing light-activated polypeptides, without limitation, are shown in FIG. 6. In some embodiments, the light-activated polypeptide hyperpolarizes the neuron when activated by light of an activating wavelength. Suitable hyperpolarizing light-activated polypeptides, without limitation, are shown in FIG. 7.

Suitable hyperpolarizing and depolarizing polypeptides are known in the art and include, e.g., a channelrhodopsin (e.g., ChR2), variants of ChR2 (e.g., C128S, D156A, C128S+D156A, E123A, E123T, iC1C2, C1C2, GtACR2, NpHR, eNpHR3.0, C1V1, VChR1, VChR2, SwiChR, Arch, ArchT, KR2, ReaChR, ChiEF, Chronos, ChRGR, and the like. Hyperpolarizing and depolarizing opsins have been described in various publications; see, e.g., Berndt and Deisseroth (2015) Science, 349:590; Berndt et al. (2014) Science, 344:420; and Guru et al. (Jul. 25, 2015) *Intl. J. Neuropsychopharmacol., pp.* 1-8 (PMID 26209858).

In some cases, a light-activated polypeptide comprises an amino acid sequence having at least 80%, at least 85%, at least 90%, at least 95%, at least 98%, at least 99%, or 100%, amino acid sequence identity to an opsin amino acid sequence depicted in FIG. 6. In some cases, a light-activated polypeptide comprises an amino acid sequence having at least 80%, at least 85%, at least 90%, at least 95%, at least 98%, at least 99%, or 100%, amino acid sequence identity to an opsin amino acid sequence depicted in FIG. 7.

In some embodiments, the light-activated polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-activated protein transport to the plasma membranes of mammalian cells can be fused to the N-terminus, the C-terminus, or to both the N- and C-terminal ends of the light-activated polypeptide. In some cases, the one or more amino acid sequence motifs which enhance light-activated polypeptide transport to the plasma membranes of mammalian cells is fused internally within a light-activated polypeptide. Optionally, the light-activated polypeptide and the one or more amino acid sequence motifs may be separated by a linker.

In some embodiments, the light-activated polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:27). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:27).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

ER export sequences that are suitable for use with a light-activated polypeptide include, e.g., VXXSL (where X is any amino acid; SEQ ID NO:28) (e.g., VKESL (SEQ ID NO:29); VLGSL (SEQ ID NO:30); etc.); NANSFCYENEVALTSK (SEQ ID NO:31); FXYENE (SEQ ID NO:32) (where X is any amino acid), e.g., FCYENEV (SEQ ID NO:33); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some cases, a light-activated polypeptide is a fusion polypeptide that comprises an endoplasmic reticulum (ER) export signal (e.g., FCYENEV; SEQ ID NO:33). In some cases, a light-activated polypeptide is a fusion polypeptide that comprises a membrane trafficking signal (e.g., KSRITSEGEYIPLDQIDINV; SEQ ID NO:27).

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-42 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A genetically encoded calcium indicator (GECI) comprising, in order from N-terminus to C-terminus: a) a calmodulin-binding polypeptide; b) a fluorescent polypeptide; and c) a calmodulin polypeptide, wherein the GECI comprises an amino acid sequence having at least 80%, at least 85%, at least 90%, at least 95%, at least 98%, at least 99%, or 100%, amino acid sequence identity to the amino acid sequence set forth in SEQ ID NO:1 wherein the GECI comprises an aspartic acid at an amino acid position corresponding to amino acid 217 of SEQ ID NO:1, and wherein the GECI has a length of from about 415 amino acids to about 440 amino acids.

Aspect 2. The GECI of aspect 1, wherein the calmodulin-binding polypeptide has a length of from 130 amino acids to 135 amino acids and comprises an amino acid sequence having at least 80%, at least 85%, at least 90%, at least 95%, at least 98%, at least 99%, or 100%, amino acid sequence identity to the following amino acid sequence:

(SEQ ID NO: 34)
MVDSSRRKWNKAGHAVRAIGRLSSPVVSERMYPEDGALKSEIKKGLRLKD

GGHYAAEVKTTYKAKKPVQLPGAYIVDIKLDIVSHNEDYTIVEQCERAEG

RHSTGGMDELYKGGTGGSLVSKGEEDNMAII.

Aspect 3. The GECI of aspect 1, wherein the calmodulin-binding polypeptide has a length of 131 amino acids and comprises an amino acid sequence having at least 90%, at least 95%, at least 98%, at least 99%, or 100%, amino acid sequence identity to the following amino acid sequence:

(SEQ ID NO: 34)
MVDSSRRKWNKAGHAVRAIGRLSSPVVSERMYPEDGALKSEIKKGLRLKD

GGHYAAEVKTTYKAKKPVQLPGAYIVDIKLDIVSHNEDYTIVEQCERAEG

RHSTGGMDELYKGGTGGSLVSKGEEDNMAII.

Aspect 4. The GECI of any one of aspects 1-3, wherein the calmodulin polypeptide has a length of from about 145 amino acids to about 150 amino acids, and comprises an amino acid sequence having at least 80%, at least 85%, at least 90%, at least 95%, at least 98%, at least 99%, or 100%, amino acid sequence identity to the following amino acid sequence:

(SEQ ID NO: 35)
DDLTEEQIAEFKEAFSLFDKDGDGTITTKELGTVFRSLGQNPTEAELQDM

INEVDADGDGTFDFPEFLTMMARKMNDTDSEEEIREAFRVFDKDGNGYIG

AAELRHVMTDLGEKLTDEEVDEMIRVADIDGDGQVNYEEFVQMMTAK.

Aspect 5. The GECI of aspect 4, wherein the calmodulin polypeptide comprises an Asp→Gln substitution at an amino acid corresponding to D272 of the amino acid sequence set forth in SEQ ID NO:1.

Aspect 6. The GECI of aspect 4 or aspect 5, wherein the calmodulin polypeptide comprises a Phe→Met substitution at an amino acid corresponding to F305 of the amino acid sequence set forth in SEQ ID NO:1.

Aspect 7. The GECI of any one of aspects 4-6, wherein the calmodulin polypeptide comprises a Phe→Leu substitution at an amino acid corresponding to F305 of the amino acid sequence set forth in SEQ ID NO:1.

Aspect 8. The GECI of any one of aspects 4-7, wherein the calmodulin polypeptide comprises an Ile→Met substitution at an amino acid corresponding to I296 of the amino acid sequence set forth in SEQ ID NO:1.

Aspect 9. The GECI of any one of aspects 4-8, wherein the calmodulin polypeptide comprises a Leu→Ile substitution at an amino acid corresponding to L385 of the amino acid sequence set forth in SEQ ID NO:1.

Aspect 10. The GECI of any one of aspects 1-9, wherein the Glu-217 is substituted with aspartic acid at position 217 (E217D).

Aspect 11. The GECI of any one of aspects 1-10, wherein the GECI further comprises a substitution of Glu-267.

Aspect 12. The GECI of aspect 11, wherein the Glu-265 is substituted with aspartic acid at position 267 (E267D).

Aspect 13. The GECI of any one of aspects 1-12, wherein the GECI further comprises a substitution of Trp-216.

Aspect 14. The GECI of aspect 13, wherein the Trp-216 is substituted with glutamine at position 216 (W216Q).

Aspect 15. The GECI of any one of aspects 1-14, wherein the fluorescent polypeptide comprises an amino acid sequence having at least 80%, at least 85%, at least 90%, at least 95%, at least 98%, at least 99%, or 100%, amino acid sequence identity to the following amino acid sequence: KEFMRFKVHMEGSVNGHEFEIEGEGEGRP-YEAFQTAKLKVTKGGPLPFAWDILSPQFMY GSKAY-IKHPADIPDYFKLSFPEGF RWDRVMNFEDGGIIHVNQDSSLQDGVFIYKVKLRG TNFPPDGPVMQKKTMGWEATR (SEQ ID NO:36), where amino acid 86 is an aspartic acid.

Aspect 16. A nucleic acid comprising a nucleotide sequence encoding the GECI of any one of aspects 1-15.

Aspect 17. A recombinant expression vector comprising the nucleic acid of aspect 16.

Aspect 18. A genetically modified host cell genetically modified with the nucleic acid of aspect 9 or the recombinant expression vector of aspect 17.

Aspect 19. The genetically modified host cell of aspect 18, wherein the host cell is a eukaryotic cell.

Aspect 20. The genetically modified host cell of aspect 17 or aspect 18, wherein the host cell is in vitro.

Aspect 21. The genetically modified host cell of any one of aspects 18-20, wherein the host cell is a neuron, a muscle cell, or a cardiac cell.

Aspect 22. The genetically modified host cell of any one of aspects 18-21, wherein the host cell is genetically modified with a nucleic acid comprising a nucleotide sequence encoding a light-activated polypeptide.

Aspect 23. The genetically modified host cell of aspect 22, wherein the light-activated polypeptide is a hyperpolarizing opsin.

Aspect 24. The genetically modified host cell of aspect 22, wherein the light-activated polypeptide is a depolarizing opsin.

Aspect 25. A method of detecting a change in intracellular calcium concentration in a eukaryotic cell, the method comprising: a) exposing the cell to a stimulant, wherein the cell comprises the GECI of any one of aspects 1-15; and b) detecting fluorescence emitted by the cell.

Aspect 26. The method of aspect 25, wherein the stimulant is a ligand for a receptor present on or in the cell.

Aspect 27. The method of aspect 25, wherein the stimulant is an electrical stimulus.

Aspect 28. The method of aspect 25, wherein the stimulant is light.

Aspect 29. The method of aspect 25, wherein the detecting step comprises imaging.

Aspect 30. The method of aspect 29, wherein imaging of the GECI is detected by fiber photometry or by two-photon microscopy.

Aspect 31. The method of any one of aspects 25-28, wherein the exposing step is performed in vivo.

Aspect 32. The method of any one of aspects 25-30, wherein the exposing step is performed in vitro.

Aspect 33. The method of aspect 32, wherein the cell is in a biological sample from a subject.

Aspect 34. The method of aspect 33, wherein the subject is a human or a non-human animal.

Aspect 35. The method of any one of aspects 25-34, wherein the cell is a brain cell.

Aspect 36. The method of aspect 35, wherein the cell is a motor neuron, a trigeminal neuron, or an ASH neuron.

Aspect 37. The method of aspect 36, wherein the motor neuron comprises terminals in the neuro-muscular junction.

Aspect 38. The method of any one of aspects 25-35, wherein the cell is a neuronal cell, a muscle cell, or a cardiomyocyte.

Aspect 39. A method of monitoring an activity of a cell, the method comprising: (i) stimulating a cell comprising the GECI polypeptide of any one of aspects 1-15; and (ii) detecting fluorescence emitted by the cell.

Aspect 40. A calcium indicator polypeptide comprising: a) a fluorescent polypeptide having a length of from about 135 amino acids to about 145 amino acids and comprising an amino acid sequence having at least 80%, at least 85%, at least 90%, at least 95%, at least 98%, at least 99%, or 100%, amino acid sequence identity to the following amino acid sequence: KEFMRFKVHMEGSVNGHE-FEIEGEGEGRPYEAFQTAKLKVTKGGPLPFAWDIL-SPQFMY GSKAYIKHPADIPDYFKLSFPEGF RWDRVMNFEDGGIIHVNQDSSLQDGVFIYKVKLRG TNFPPDGPVMQKKTMGWEATR (SEQ ID NO:36), where amino acid 86 is an aspartic acid; and b) a calcium-binding polypeptide.

Aspect 41. The calcium indicator polypeptide of aspect 40, wherein the calcium-binding polypeptide is calmodulin and wherein the calcium indicator polypeptide comprises a calmodulin-binding polypeptide having a length of from 130 amino acids to 135 amino acids and comprising an amino acid sequence having at least 80%, at least 85%, at least 90%, at least 95%, at least 98%, at least 99%, or 100%, amino acid sequence identity to the following amino acid sequence:

(SEQ ID NO: 34)
MVDSSRRKWNKAGHAVRAIGRLSSPVVSERMYPEDGALKSEIKKGLRLKD

GGHYAAEVKTTYKAKKPVQLPGAYIVDIKLDIVSHNEDYTIVEQCERAEG

RHSTGGMDELYKGGTGGSLVSKGEEDNMAII;

Aspect 42. The calcium indicator polypeptide of aspect 40, wherein the calcium-binding polypeptide is a troponin C polypeptide.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Cytosolic Red Calcium Indicator

There are 2 'WE' motifs in the jrGECO 1a sequence (SEQ ID NO:2). One at position 217 and another at position 267. Each glutamic acid was mutated to aspartic acid either individually or in tandem and the cellular expression observed for all three constructs, 217D, 267D and 217D/267D. Only the truncated jrGECO with the 217D mutation showed an aggregate free expression. The improved red GECI was renamed sRGECO (GECI). Kinetic studies were performed on neurons expressing GECI to determine baseline fluorescence, decay kinetics, signal to noise ratio, and changes in the signal amplitude. By all four parameters, the GECI was far superior as compared to the jrGECO 1a (amino acid sequence set forth in FIG. 2; SEQ ID NO:2).

FIG. 1 provides the amino acid sequence of a GECI (SEQ ID NO:1).

FIG. 2 provides the amino acid sequence of jrGECO 1a (SEQ ID NO:2).

FIG. 3 shows a comparison of the excitation trace of jRGECO1-E217D (GECI with a substitution of an amino acid corresponding to Glu-217 to 217D) to jRGECO.

Figure 4:
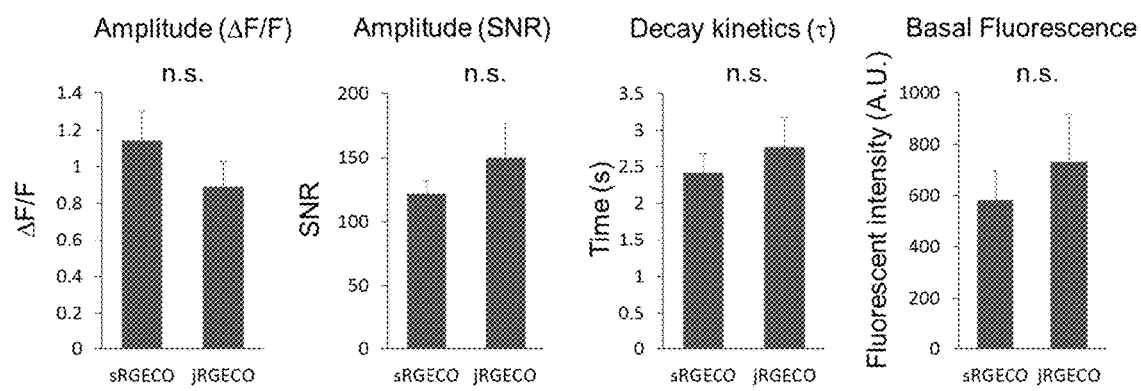
FIG. 4 shows the kinetic studies performed on primary hippocampal culture expressing jRGECO1-E217D (GECI) compared to jRGECO1 to determine base-line fluorescence, decay kinetics, signal to noise ratio, and changes in the signal amplitude.

FIG. 4 shows the kinetic studies performed on primary hippocampal culture expressing jRGECO1-E217D (GECI) compared to jRGECO1 to determine base-line fluorescence, decay kinetics, signal to noise ratio, and changes in the signal amplitude. Error bar indicates SEM. jRGECO1-E217D (n=23), jRGECO1 (n=21). N.s. in t-test.

Figure 5:
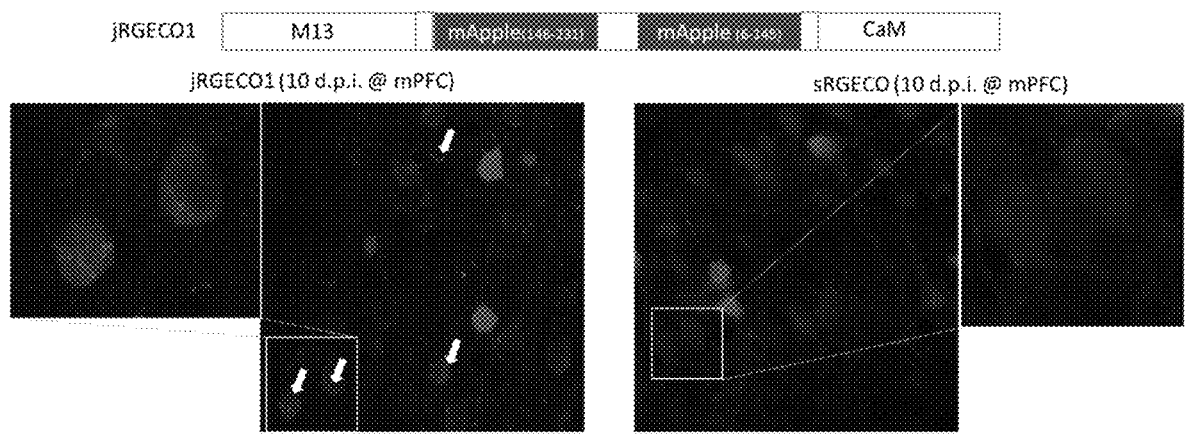
FIG. 5 illustrates the fluorescence signal of GECI compared to jRGECO1 (wild-type).

FIG. 5 illustrates the fluorescence signal of GECI compared to jRGECO1 (wild-type).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically encoded calcium indicator (GECI) as set forth in SEQ ID NO: 1, wherein there is an aspartic acid at an amino acid position corresponding to amino acid 217 of SEQ ID NO:1; or a variant thereof, wherein the variant comprises a calmodulin polypeptide comprising one or more of:
   a) an Asp→Gln substitution at position D272;
   b) a Phe→Met substitution at an amino acid corresponding to F305 of the amino acid sequence set forth in SEQ ID NO: 1;
   c) a Phe→Leu substitution at an amino acid corresponding to F305 of the amino acid sequence set forth in SEQ ID NO: 1;
   d) an Ile→Met substitution at an amino acid corresponding to I296 of the amino acid sequence set forth in SEQ ID NO: 1; and
   e) a Leu→Ile substitution at an amino acid corresponding to L385 of the amino acid sequence set forth in SEQ ID NO: 1.

2. The GECI of claim 1, wherein the GECI further comprises a substitution of Glu-267.

3. The GECI of claim 2, wherein the Glu-267 is substituted with aspartic acid at position 267 (E267D).

4. The GECI of claim 2, wherein the GECI further comprises a substitution of Trp-216.

5. The GECI of claim 4, wherein the Trp-216 is substituted with glutamine at position 216 (W216Q).

6. A nucleic acid comprising a nucleotide sequence encoding the GECI of claim 1.

7. A genetically modified host cell genetically modified with the nucleic acid of claim 6.

8. The genetically modified host cell of claim 7, wherein the host cell is a eukaryotic cell.

9. The genetically modified host cell of claim 7, wherein the host cell is genetically modified with a nucleic acid comprising a nucleotide sequence encoding a light-activated polypeptide.

10. The genetically modified host cell of claim 9, wherein the light-activated polypeptide is a hyperpolarizing opsin.

11. The genetically modified host cell of claim 9, wherein the light-activated polypeptide is a depolarizing opsin.

12. A method of detecting a change in intracellular calcium concentration in a eukaryotic cell, the method comprising:
   a) exposing the cell to a stimulant, wherein the cell comprises the GECI of claim 1 and wherein the stimulant is selected from the group consisting of a ligand for a receptor present on or in the cell, an electrical stimulus, and light; and
   b) detecting fluorescence emitted by the cell.

13. The method of claim 12, wherein the detecting step comprises imaging of the GECI by fiber photometry or by two-photon microscopy.

14. The method of claim 12, wherein the exposing step is performed in vivo or in vitro.

15. The method of claim 12, wherein the cell is a brain cell.

16. The method of claim 15, wherein the cell is a motor neuron, a trigeminal neuron, or an ASH neuron.

17. The method of claim 12, wherein the cell is a neuronal cell, a muscle cell, or a cardiomyocyte.

18. A method of monitoring an activity of a cell, the method comprising:
   (i) stimulating a cell comprising the GECI polypeptide of claim 1 by exposing the cell to a stimulant, wherein the cell comprises the GECI of claim 1 and wherein the stimulant is selected from the group consisting of a ligand for a receptor present on or in the cell, an electrical stimulus, and light; and
   (ii) detecting fluorescence emitted by the cell.

* * * * *

SEQUENCE LISTING

<160> NUMBER OF SEQ ID NOS: 87

<210> SEQ ID NO 1
<211> LENGTH: 417
<212> TYPE: PRT
<213> ORGANISM: Artificial sequence
<220> FEATURE:
<223> OTHER INFORMATION: synthetic sequence

<400> SEQUENCE: 1

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
    50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
        115                 120                 125

Ala Ile Ile Lys Glu Phe Met Arg Phe Lys Val His Met Glu Gly Ser
    130                 135                 140

Val Asn Gly His Glu Phe Glu Ile Glu Gly Glu Gly Glu Gly Arg Pro
145                 150                 155                 160

Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
            180                 185                 190

Lys Ala Tyr Ile Lys His Pro Ala Asp Ile Pro Asp Tyr Phe Lys Leu
        195                 200                 205

Ser Phe Pro Glu Gly Phe Arg Trp Asp Arg Val Met Asn Phe Glu Asp
    210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Ala Thr Arg Asp Asp
            260                 265                 270

Leu Thr Glu Glu Gln Ile Ala Glu Phe Lys Glu Ala Phe Ser Leu Phe
        275                 280                 285

Asp Lys Asp Gly Asp Gly Thr Ile Thr Thr Lys Glu Leu Gly Thr Val
    290                 295                 300

Phe Arg Ser Leu Gly Gln Asn Pro Thr Glu Ala Glu Leu Gln Asp Met
305                 310                 315                 320

Ile Asn Glu Val Asp Ala Asp Gly Asp Gly Thr Phe Asp Phe Pro Glu
                325                 330                 335

Phe Leu Thr Met Met Ala Arg Lys Met Asn Asp Thr Asp Ser Glu Glu
            340                 345                 350

Glu Ile Arg Glu Ala Phe Arg Val Phe Asp Lys Asp Gly Asn Gly Tyr

```
                355                 360                 365
Ile Gly Ala Ala Glu Leu Arg His Val Met Thr Asp Leu Gly Glu Lys
    370                 375                 380
Leu Thr Asp Glu Glu Val Asp Glu Met Ile Arg Val Ala Asp Ile Asp
385                 390                 395                 400
Gly Asp Gly Gln Val Asn Tyr Glu Glu Phe Val Gln Met Met Thr Ala
                405                 410                 415
Lys

<210> SEQ ID NO 2
<211> LENGTH: 451
<212> TYPE: PRT
<213> ORGANISM: Artificial sequence
<220> FEATURE:
<223> OTHER INFORMATION: synthetic sequence

<400> SEQUENCE: 2

Met Gly Ser His His His His His Gly Met Ala Ser Met Thr Gly
1               5                   10                  15
Gly Gln Gln Met Gly Arg Asp Leu Tyr Asp Asp Asp Lys Asp Leu
                20                  25                  30
Ala Thr Met Val Asp Ser Ser Arg Arg Lys Trp Asn Lys Ala Gly His
            35                  40                  45
Ala Val Arg Ala Ile Gly Arg Leu Ser Ser Pro Val Val Ser Glu Arg
        50                  55                  60
Met Tyr Pro Glu Asp Gly Ala Leu Lys Ser Glu Ile Lys Lys Gly Leu
65                  70                  75                  80
Arg Leu Lys Asp Gly His Tyr Ala Ala Glu Val Lys Thr Thr Tyr
                85                  90                  95
Lys Ala Lys Lys Pro Val Gln Leu Pro Gly Ala Tyr Ile Val Asp Ile
            100                 105                 110
Lys Leu Asp Ile Val Ser His Asn Glu Asp Tyr Thr Ile Val Glu Gln
        115                 120                 125
Cys Glu Arg Ala Glu Gly Arg His Ser Thr Gly Gly Met Asp Glu Leu
    130                 135                 140
Tyr Lys Gly Gly Thr Gly Gly Ser Leu Val Ser Lys Gly Glu Glu Asp
145                 150                 155                 160
Asn Met Ala Ile Ile Lys Glu Phe Met Arg Phe Lys Val His Met Glu
                165                 170                 175
Gly Ser Val Asn Gly His Glu Phe Glu Ile Glu Gly Glu Gly Glu Gly
            180                 185                 190
Arg Pro Tyr Glu Ala Phe Gln Thr Ala Lys Leu Lys Val Thr Lys Gly
        195                 200                 205
Gly Pro Leu Pro Phe Ala Trp Asp Ile Leu Ser Pro Gln Phe Met Tyr
    210                 215                 220
Gly Ser Lys Ala Tyr Ile Lys His Pro Ala Asp Ile Pro Asp Tyr Phe
225                 230                 235                 240
Lys Leu Ser Phe Pro Glu Gly Phe Arg Trp Glu Arg Val Met Asn Phe
                245                 250                 255
Glu Asp Gly Gly Ile Ile His Val Asn Gln Asp Ser Ser Leu Gln Asp
            260                 265                 270
Gly Val Phe Ile Tyr Lys Val Lys Leu Arg Gly Thr Asn Phe Pro Pro
        275                 280                 285
Asp Gly Pro Val Met Gln Lys Lys Thr Met Gly Trp Glu Ala Thr Arg
    290                 295                 300
```

Asp Asp Leu Thr Glu Glu Gln Ile Ala Glu Phe Lys Glu Ala Phe Ser
305                 310                 315                 320

Leu Phe Asp Lys Asp Gly Asp Gly Thr Ile Thr Thr Lys Glu Leu Gly
                325                 330                 335

Thr Val Phe Arg Ser Leu Gly Gln Asn Pro Thr Glu Ala Glu Leu Gln
                340                 345                 350

Asp Met Ile Asn Glu Val Asp Ala Asp Gly Asp Gly Thr Phe Asp Phe
                355                 360                 365

Pro Glu Phe Leu Thr Met Met Ala Arg Lys Met Asn Asp Thr Asp Ser
370                 375                 380

Glu Glu Glu Ile Arg Glu Ala Phe Arg Val Phe Asp Lys Asp Gly Asn
385                 390                 395                 400

Gly Tyr Ile Gly Ala Ala Glu Leu Arg His Val Met Thr Asp Leu Gly
                405                 410                 415

Glu Lys Leu Thr Asp Glu Glu Val Asp Glu Met Ile Arg Val Ala Asp
                420                 425                 430

Ile Asp Gly Asp Gly Gln Val Asn Tyr Glu Glu Phe Val Gln Met Met
                435                 440                 445

Thr Ala Lys
   450

<210> SEQ ID NO 3
<211> LENGTH: 139
<212> TYPE: PRT
<213> ORGANISM: Artificial sequence
<220> FEATURE:
<223> OTHER INFORMATION: synthetic sequence

<400> SEQUENCE: 3

Lys Glu Phe Met Arg Phe Lys Val His Met Glu Gly Ser Val Asn Gly
1               5                   10                  15

His Glu Phe Glu Ile Glu Gly Glu Gly Glu Gly Arg Pro Tyr Glu Ala
                20                  25                  30

Phe Gln Thr Ala Lys Leu Lys Val Thr Lys Gly Gly Pro Leu Pro Phe
                35                  40                  45

Ala Trp Asp Ile Leu Ser Pro Gln Phe Met Tyr Gly Ser Lys Ala Tyr
        50                  55                  60

Ile Lys His Pro Ala Asp Ile Pro Asp Tyr Phe Lys Leu Ser Phe Pro
65                  70                  75                  80

Glu Gly Phe Arg Trp Asp Arg Val Met Asn Phe Glu Asp Gly Gly Ile
                85                  90                  95

Ile His Val Asn Gln Asp Ser Ser Leu Gln Asp Gly Val Phe Ile Tyr
                100                 105                 110

Lys Val Lys Leu Arg Gly Thr Asn Phe Pro Pro Asp Gly Pro Val Met
                115                 120                 125

Gln Lys Lys Thr Met Gly Trp Glu Ala Thr Arg
            130                 135

<210> SEQ ID NO 4
<211> LENGTH: 139
<212> TYPE: PRT
<213> ORGANISM: Artificial sequence
<220> FEATURE:
<223> OTHER INFORMATION: synthetic sequence

<400> SEQUENCE: 4

Lys Glu Phe Met Arg Phe Lys Val His Met Glu Gly Ser Val Asn Gly

```
                1               5                  10                 15
            His Glu Phe Glu Ile Glu Gly Glu Gly Glu Gly Arg Pro Tyr Glu Ala
                            20                  25                 30

Phe Gln Thr Ala Lys Leu Lys Val Thr Lys Gly Gly Pro Leu Pro Phe
                            35                  40                 45

Ala Trp Asp Ile Leu Ser Pro Gln Phe Met Tyr Gly Ser Lys Ala Tyr
                50                          55                  60

Ile Lys His Pro Ala Asp Ile Pro Asp Tyr Phe Lys Leu Ser Phe Pro
            65                  70                  75                 80

Glu Gly Phe Arg Trp Asp Arg Val Met Asn Phe Glu Asp Gly Gly Ile
                            85                  90                  95

Ile His Val Asn Gln Asp Ser Ser Leu Gln Asp Gly Val Phe Ile Tyr
                            100                 105                110

Lys Val Lys Leu Arg Gly Thr Asn Phe Pro Pro Asp Gly Pro Val Met
                            115                 120                125

Gln Lys Lys Thr Met Gly Trp Glu Ala Thr Arg
                            130                 135

<210> SEQ ID NO 5
<211> LENGTH: 139
<212> TYPE: PRT
<213> ORGANISM: Artificial sequence
<220> FEATURE:
<223> OTHER INFORMATION: synthetic sequence

<400> SEQUENCE: 5

Lys Glu Phe Met Arg Phe Lys Val His Met Glu Gly Ser Val Asn Gly
            1               5                  10                  15

His Glu Phe Glu Ile Glu Gly Glu Gly Glu Gly Arg Pro Tyr Glu Ala
                            20                  25                 30

Phe Gln Thr Ala Lys Leu Lys Val Thr Lys Gly Gly Pro Leu Pro Phe
                            35                  40                 45

Ala Trp Asp Ile Leu Ser Pro Gln Phe Met Tyr Gly Ser Lys Ala Tyr
                50                          55                  60

Ile Lys His Pro Ala Asp Ile Pro Asp Tyr Phe Lys Leu Ser Phe Pro
            65                  70                  75                 80

Glu Gly Phe Arg Trp Asp Arg Val Met Asn Phe Glu Asp Gly Gly Ile
                            85                  90                  95

Ile His Val Asn Gln Asp Ser Ser Leu Gln Asp Gly Val Phe Ile Tyr
                            100                 105                110

Lys Val Lys Leu Arg Gly Thr Asn Phe Pro Pro Asp Gly Pro Val Met
                            115                 120                125

Gln Lys Lys Thr Met Gly Trp Glu Ala Thr Arg
                            130                 135

<210> SEQ ID NO 6
<211> LENGTH: 139
<212> TYPE: PRT
<213> ORGANISM: Artificial sequence
<220> FEATURE:
<223> OTHER INFORMATION: synthetic sequence

<400> SEQUENCE: 6

Lys Glu Phe Met Arg Phe Lys Val His Met Glu Gly Ser Val Asn Gly
            1               5                  10                  15

His Glu Phe Glu Ile Glu Gly Glu Gly Glu Gly Arg Pro Tyr Glu Ala
                            20                  25                 30
```

```
Phe Gln Thr Ala Lys Leu Lys Val Thr Lys Gly Gly Pro Leu Pro Phe
            35                  40                  45

Ala Trp Asp Ile Leu Ser Pro Gln Phe Met Tyr Gly Ser Lys Ala Tyr
 50                  55                  60

Ile Lys His Pro Ala Asp Ile Pro Asp Tyr Phe Lys Leu Ser Phe Pro
 65                  70                  75                  80

Glu Gly Phe Arg Trp Asp Arg Val Met Asn Phe Glu Asp Gly Gly Ile
                 85                  90                  95

Ile His Val Asn Gln Asp Ser Ser Leu Gln Asp Gly Val Phe Ile Tyr
                100                 105                 110

Lys Val Lys Leu Arg Gly Thr Asn Phe Pro Pro Asp Gly Pro Val Met
            115                 120                 125

Gln Lys Lys Thr Met Gly Trp Glu Ala Thr Arg
            130                 135

<210> SEQ ID NO 7
<211> LENGTH: 139
<212> TYPE: PRT
<213> ORGANISM: Artificial sequence
<220> FEATURE:
<223> OTHER INFORMATION: synthetic sequence

<400> SEQUENCE: 7

Lys Glu Phe Met Arg Phe Lys Val His Met Glu Gly Ser Val Asn Gly
 1               5                  10                  15

His Glu Phe Glu Ile Glu Gly Glu Gly Glu Gly Arg Pro Tyr Glu Ala
                20                  25                  30

Phe Gln Thr Ala Lys Leu Lys Val Thr Lys Gly Gly Pro Leu Pro Phe
            35                  40                  45

Ala Trp Asp Ile Leu Ser Pro Gln Phe Met Tyr Gly Ser Lys Ala Tyr
 50                  55                  60

Ile Lys His Pro Ala Asp Ile Pro Asp Tyr Phe Lys Leu Ser Phe Pro
 65                  70                  75                  80

Glu Gly Phe Arg Gln Asp Arg Val Met Asn Phe Glu Asp Gly Gly Ile
                 85                  90                  95

Ile His Val Asn Gln Asp Ser Ser Leu Gln Asp Gly Val Phe Ile Tyr
                100                 105                 110

Lys Val Lys Leu Arg Gly Thr Asn Phe Pro Pro Asp Gly Pro Val Met
            115                 120                 125

Gln Lys Lys Thr Met Gly Trp Glu Ala Thr Arg
            130                 135

<210> SEQ ID NO 8
<211> LENGTH: 139
<212> TYPE: PRT
<213> ORGANISM: Artificial sequence
<220> FEATURE:
<223> OTHER INFORMATION: synthetic sequence

<400> SEQUENCE: 8

Lys Glu Phe Met Arg Phe Lys Val His Met Glu Gly Ser Val Asn Gly
 1               5                  10                  15

His Glu Phe Glu Ile Glu Gly Glu Gly Glu Gly Arg Pro Tyr Glu Ala
                20                  25                  30

Phe Gln Thr Ala Lys Leu Lys Val Thr Lys Gly Gly Pro Leu Pro Phe
            35                  40                  45

Ala Trp Asp Ile Leu Ser Pro Gln Phe Met Tyr Gly Ser Lys Ala Tyr
 50                  55                  60
```

Ile Lys His Pro Ala Asp Ile Pro Asp Tyr Phe Lys Leu Ser Phe Pro
65                  70                  75                  80

Glu Gly Phe Arg Gln Asp Arg Val Met Asn Phe Glu Asp Gly Gly Ile
                85                  90                  95

Ile His Val Asn Gln Asp Ser Ser Leu Gln Asp Gly Val Phe Ile Tyr
            100                 105                 110

Lys Val Lys Leu Arg Gly Thr Asn Phe Pro Pro Asp Gly Pro Val Met
        115                 120                 125

Gln Lys Lys Thr Met Gly Trp Glu Ala Thr Arg
    130                 135

<210> SEQ ID NO 9
<211> LENGTH: 139
<212> TYPE: PRT
<213> ORGANISM: Artificial sequence
<220> FEATURE:
<223> OTHER INFORMATION: synthetic sequence

<400> SEQUENCE: 9

Lys Glu Phe Met Arg Phe Lys Val His Met Glu Gly Ser Val Asn Gly
1               5                   10                  15

His Glu Phe Glu Ile Glu Gly Glu Gly Arg Pro Tyr Glu Ala
                20                  25                  30

Phe Gln Thr Ala Lys Leu Lys Val Thr Lys Gly Gly Pro Leu Pro Phe
            35                  40                  45

Ala Trp Asp Ile Leu Ser Pro Gln Phe Met Tyr Gly Ser Lys Ala Tyr
        50                  55                  60

Ile Lys His Pro Ala Asp Ile Pro Asp Tyr Phe Lys Leu Ser Phe Pro
65                  70                  75                  80

Glu Gly Phe Arg Gln Asp Arg Val Met Asn Phe Glu Asp Gly Gly Ile
                85                  90                  95

Ile His Val Asn Gln Asp Ser Ser Leu Gln Asp Gly Val Phe Ile Tyr
            100                 105                 110

Lys Val Lys Leu Arg Gly Thr Asn Phe Pro Pro Asp Gly Pro Val Met
        115                 120                 125

Gln Lys Lys Thr Met Gly Trp Glu Ala Thr Arg
    130                 135

<210> SEQ ID NO 10
<211> LENGTH: 139
<212> TYPE: PRT
<213> ORGANISM: Artificial sequence
<220> FEATURE:
<223> OTHER INFORMATION: synthetic sequence

<400> SEQUENCE: 10

Lys Glu Phe Met Arg Phe Lys Val His Met Glu Gly Ser Val Asn Gly
1               5                   10                  15

His Glu Phe Glu Ile Glu Gly Glu Gly Arg Pro Tyr Glu Ala
                20                  25                  30

Phe Gln Thr Ala Lys Leu Lys Val Thr Lys Gly Gly Pro Leu Pro Phe
            35                  40                  45

Ala Trp Asp Ile Leu Ser Pro Gln Phe Met Tyr Gly Ser Lys Ala Tyr
        50                  55                  60

Ile Lys His Pro Ala Asp Ile Pro Asp Tyr Phe Lys Leu Ser Phe Pro
65                  70                  75                  80

Glu Gly Phe Arg Gln Asp Arg Val Met Asn Phe Glu Asp Gly Gly Ile

```
                    85                  90                  95

Ile His Val Asn Gln Asp Ser Ser Leu Gln Asp Gly Val Phe Ile Tyr
                100                 105                 110

Lys Val Lys Leu Arg Gly Thr Asn Phe Pro Pro Asp Gly Pro Val Met
        115                 120                 125

Gln Lys Lys Thr Met Gly Trp Glu Ala Thr Arg
    130                 135

<210> SEQ ID NO 11
<211> LENGTH: 147
<212> TYPE: PRT
<213> ORGANISM: Artificial sequence
<220> FEATURE:
<223> OTHER INFORMATION: synthetic sequence

<400> SEQUENCE: 11

Asp Asp Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Phe Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
                100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 12
<211> LENGTH: 147
<212> TYPE: PRT
<213> ORGANISM: Artificial sequence
<220> FEATURE:
<223> OTHER INFORMATION: synthetic sequence

<400> SEQUENCE: 12

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Phe Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95
```

```
Gly Tyr Ile Gly Ala Ala Glu Leu Arg His Val Met Thr Asp Leu Gly
            100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 13
<211> LENGTH: 147
<212> TYPE: PRT
<213> ORGANISM: Artificial sequence
<220> FEATURE:
<223> OTHER INFORMATION: synthetic sequence

<400> SEQUENCE: 13

Asp Asp Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
            100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 14
<211> LENGTH: 147
<212> TYPE: PRT
<213> ORGANISM: Artificial sequence
<220> FEATURE:
<223> OTHER INFORMATION: synthetic sequence

<400> SEQUENCE: 14

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95
```

```
Gly Tyr Ile Gly Ala Ala Glu Leu Arg His Val Met Thr Asp Leu Gly
            100                 105                 110

Glu Lys Leu Thr Asp Glu Val Asp Glu Met Ile Arg Val Ala Asp
        115                 120                 125

Ile Asp Gly Asp Gly Gln Val Asn Tyr Glu Glu Phe Val Gln Met Met
130                 135                 140

Thr Ala Lys
145

<210> SEQ ID NO 15
<211> LENGTH: 147
<212> TYPE: PRT
<213> ORGANISM: Artificial sequence
<220> FEATURE:
<223> OTHER INFORMATION: synthetic sequence

<400> SEQUENCE: 15

Asp Asp Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Leu Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
            100                 105                 110

Glu Lys Leu Thr Asp Glu Val Asp Glu Met Ile Arg Val Ala Asp
        115                 120                 125

Ile Asp Gly Asp Gly Gln Val Asn Tyr Glu Glu Phe Val Gln Met Met
130                 135                 140

Thr Ala Lys
145

<210> SEQ ID NO 16
<211> LENGTH: 147
<212> TYPE: PRT
<213> ORGANISM: Artificial sequence
<220> FEATURE:
<223> OTHER INFORMATION: synthetic sequence

<400> SEQUENCE: 16

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Leu Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
```

```
                    85                  90                  95
Gly Tyr Ile Gly Ala Ala Glu Leu Arg His Val Met Thr Asp Leu Gly
                100                 105                 110

Glu Lys Leu Thr Asp Glu Glu Val Asp Glu Met Ile Arg Val Ala Asp
            115                 120                 125

Ile Asp Gly Asp Gly Gln Val Asn Tyr Glu Glu Phe Val Gln Met Met
        130                 135                 140

Thr Ala Lys
145

<210> SEQ ID NO 17
<211> LENGTH: 147
<212> TYPE: PRT
<213> ORGANISM: Artificial sequence
<220> FEATURE:
<223> OTHER INFORMATION: synthetic sequence

<400> SEQUENCE: 17

Asp Asp Leu Thr Glu Glu Gln Ile Ala Glu Phe Lys Glu Ala Phe Ser
1               5                   10                  15

Leu Phe Asp Lys Asp Gly Asp Gly Thr Met Thr Thr Lys Glu Leu Gly
                20                  25                  30

Thr Val Phe Arg Ser Leu Gly Gln Asn Pro Thr Glu Ala Glu Leu Gln
            35                  40                  45

Asp Met Ile Asn Glu Val Asp Ala Asp Gly Asp Gly Thr Phe Asp Phe
        50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
                100                 105                 110

Glu Lys Leu Thr Asp Glu Glu Val Asp Glu Met Ile Arg Val Ala Asp
            115                 120                 125

Ile Asp Gly Asp Gly Gln Val Asn Tyr Glu Glu Phe Val Gln Met Met
        130                 135                 140

Thr Ala Lys
145

<210> SEQ ID NO 18
<211> LENGTH: 147
<212> TYPE: PRT
<213> ORGANISM: Artificial sequence
<220> FEATURE:
<223> OTHER INFORMATION: synthetic sequence

<400> SEQUENCE: 18

Asp Asp Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
                20                  25                  30

Thr Val Phe Arg Ser Leu Gly Gln Asn Pro Thr Glu Ala Glu Leu Gln
            35                  40                  45

Asp Met Ile Asn Glu Val Asp Ala Asp Gly Asp Gly Thr Phe Asp Phe
        50                  55                  60

Pro Glu Phe Leu Thr Met Met Ala Arg Lys Met Asn Asp Thr Asp Ser
65                  70                  75                  80
```

```
Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
            100                 105                 110

Glu Lys Ile Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 19
<211> LENGTH: 131
<212> TYPE: PRT
<213> ORGANISM: Artificial sequence
<220> FEATURE:
<223> OTHER INFORMATION: synthetic sequence

<400> SEQUENCE: 19

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
    50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
        115                 120                 125

Ala Ile Ile
    130

<210> SEQ ID NO 20
<211> LENGTH: 160
<212> TYPE: PRT
<213> ORGANISM: Artificial sequence
<220> FEATURE:
<223> OTHER INFORMATION: synthetic sequence

<400> SEQUENCE: 20

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
            20                  25                  30

Gly Asp Ile Ser Val Lys Glu Leu Gly Thr Val Met Arg Met Leu Gly
        35                  40                  45

Gln Thr Pro Thr Lys Glu Glu Leu Asp Ala Ile Ile Glu Glu Val Asp
    50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95
```

```
Ala Glu Cys Phe Arg Ile Phe Asp Arg Asn Ala Asp Gly Tyr Ile Asp
            100                 105                 110

Pro Gly Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160

<210> SEQ ID NO 21
<211> LENGTH: 160
<212> TYPE: PRT
<213> ORGANISM: Artificial sequence
<220> FEATURE:
<223> OTHER INFORMATION: synthetic sequence

<400> SEQUENCE: 21

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
            20                  25                  30

Gly Asp Ile Ser Val Lys Glu Leu Gly Thr Val Met Arg Met Leu Gly
        35                  40                  45

Gln Thr Pro Thr Lys Glu Glu Leu Asp Ala Ile Ile Glu Glu Val Asp
    50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95

Ala Glu Cys Phe Arg Ile Phe Asp Arg Asp Ala Asn Gly Tyr Ile Asp
            100                 105                 110

Ala Glu Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160

<210> SEQ ID NO 22
<211> LENGTH: 160
<212> TYPE: PRT
<213> ORGANISM: Artificial sequence
<220> FEATURE:
<223> OTHER INFORMATION: synthetic sequence

<400> SEQUENCE: 22

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
            20                  25                  30

Gly Asp Ile Ser Val Lys Glu Leu Gly Thr Val Met Arg Met Leu Gly
        35                  40                  45

Gln Thr Pro Thr Lys Glu Glu Leu Asp Ala Ile Ile Glu Glu Val Asp
    50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
```

```
                85                  90                  95
Ala Glu Cys Phe Arg Ile Phe Asp Arg Asp Ala Asn Gly Tyr Ile Asp
            100                 105                 110

Ala Glu Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160
```

<210> SEQ ID NO 23
<211> LENGTH: 187
<212> TYPE: PRT
<213> ORGANISM: Artificial sequence
<220> FEATURE:
<223> OTHER INFORMATION: synthetic sequence

<400> SEQUENCE: 23

```
Met Pro Glu Val Glu Arg Lys Pro Lys Ile Thr Ala Ser Arg Lys Leu
1               5                   10                  15

Leu Leu Lys Ser Leu Met Leu Ala Lys Ala Lys Glu Cys Trp Glu Gln
            20                  25                  30

Glu His Glu Glu Arg Glu Ala Glu Lys Val Arg Tyr Leu Ala Glu Arg
        35                  40                  45

Ile Pro Thr Leu Gln Thr Arg Gly Leu Ser Leu Ser Ala Leu Gln Asp
    50                  55                  60

Leu Cys Arg Glu Leu His Ala Lys Val Glu Val Val Asp Glu Glu Arg
65                  70                  75                  80

Tyr Asp Ile Glu Ala Lys Cys Leu His Asn Thr Arg Glu Ile Lys Asp
                85                  90                  95

Leu Lys Leu Lys Val Met Asp Leu Arg Gly Lys Phe Lys Arg Pro Pro
            100                 105                 110

Leu Arg Arg Val Arg Val Ser Ala Asp Ala Met Leu Arg Ala Leu Leu
        115                 120                 125

Gly Ser Lys His Lys Val Ser Met Asp Leu Arg Ala Asn Leu Lys Ser
    130                 135                 140

Val Lys Lys Glu Asp Thr Glu Lys Glu Arg Pro Val Glu Val Gly Asp
145                 150                 155                 160

Trp Arg Lys Asn Val Glu Ala Met Ser Gly Met Gly Arg Lys Lys
                165                 170                 175

Met Phe Asp Ala Ala Lys Ser Pro Thr Ser Gln
            180                 185
```

<210> SEQ ID NO 24
<211> LENGTH: 20
<212> TYPE: PRT
<213> ORGANISM: Artificial sequence
<220> FEATURE:
<223> OTHER INFORMATION: synthetic sequence

<400> SEQUENCE: 24

```
Lys Asp Leu Lys Leu Lys Val Met Asp Leu Arg Gly Lys Phe Lys Arg
1               5                   10                  15

Pro Pro Leu Arg
            20
```

<210> SEQ ID NO 25
<211> LENGTH: 25

```
<212> TYPE: PRT
<213> ORGANISM: Artificial sequence
<220> FEATURE:
<223> OTHER INFORMATION: synthetic sequence

<400> SEQUENCE: 25

Arg Met Ser Ala Asp Ala Met Leu Lys Ala Leu Leu Gly Ser Lys His
1               5                   10                  15

Lys Val Ala Met Asp Leu Arg Ala Asn
            20                  25

<210> SEQ ID NO 26
<211> LENGTH: 44
<212> TYPE: PRT
<213> ORGANISM: Artificial sequence
<220> FEATURE:
<223> OTHER INFORMATION: synthetic sequence

<400> SEQUENCE: 26

Asn Gln Lys Leu Phe Asp Leu Arg Gly Lys Phe Lys Arg Pro Pro Leu
1               5                   10                  15

Arg Arg Val Arg Met Ser Ala Asp Ala Met Leu Lys Ala Leu Leu Gly
            20                  25                  30

Ser Lys His Lys Val Ala Met Asp Leu Arg Ala Asn
        35                  40

<210> SEQ ID NO 27
<211> LENGTH: 20
<212> TYPE: PRT
<213> ORGANISM: Artificial sequence
<220> FEATURE:
<223> OTHER INFORMATION: synthetic sequence

<400> SEQUENCE: 27

Lys Ser Arg Ile Thr Ser Glu Gly Glu Tyr Ile Pro Leu Asp Gln Ile
1               5                   10                  15

Asp Ile Asn Val
            20

<210> SEQ ID NO 28
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (2)..(3)
<223> OTHER INFORMATION: Xaa at residues 2 and 3 may be any amino acid

<400> SEQUENCE: 28

Val Xaa Xaa Ser Leu
1               5

<210> SEQ ID NO 29
<211> LENGTH: 5
<212> TYPE: PRT
<213> ORGANISM: Artificial sequence
<220> FEATURE:
<223> OTHER INFORMATION: synthetic sequence

<400> SEQUENCE: 29

Val Lys Glu Ser Leu
1               5
```

```
<210> SEQ ID NO 30
<211> LENGTH: 5
<212> TYPE: PRT
<213> ORGANISM: Artificial sequence
<220> FEATURE:
<223> OTHER INFORMATION: synthetic sequence

<400> SEQUENCE: 30

Val Leu Gly Ser Leu
1               5

<210> SEQ ID NO 31
<211> LENGTH: 16
<212> TYPE: PRT
<213> ORGANISM: Artificial sequence
<220> FEATURE:
<223> OTHER INFORMATION: synthetic sequence

<400> SEQUENCE: 31

Asn Ala Asn Ser Phe Cys Tyr Glu Asn Glu Val Ala Leu Thr Ser Lys
1               5                   10                  15

<210> SEQ ID NO 32
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa may be any amino acid.

<400> SEQUENCE: 32

Phe Xaa Tyr Glu Asn Glu
1               5

<210> SEQ ID NO 33
<211> LENGTH: 7
<212> TYPE: PRT
<213> ORGANISM: Artificial sequence
<220> FEATURE:
<223> OTHER INFORMATION: synthetic sequence

<400> SEQUENCE: 33

Phe Cys Tyr Glu Asn Glu Val
1               5

<210> SEQ ID NO 34
<211> LENGTH: 131
<212> TYPE: PRT
<213> ORGANISM: Artificial sequence
<220> FEATURE:
<223> OTHER INFORMATION: synthetic sequence

<400> SEQUENCE: 34

Met Val Asp Ser Ser Arg Arg Lys Trp Asn Lys Ala Gly His Ala Val
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
    50                  55                  60

Lys Lys Pro Val Gln Leu Pro Gly Ala Tyr Ile Val Asp Ile Lys Leu
65                  70                  75                  80
```

```
Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
        115                 120                 125

Ala Ile Ile
    130

<210> SEQ ID NO 35
<211> LENGTH: 147
<212> TYPE: PRT
<213> ORGANISM: Artificial sequence
<220> FEATURE:
<223> OTHER INFORMATION: synthetic sequence

<400> SEQUENCE: 35

Asp Asp Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Phe Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Asn Asp Thr Asp Ser
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
            100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 36
<211> LENGTH: 139
<212> TYPE: PRT
<213> ORGANISM: Artificial sequence
<220> FEATURE:
<223> OTHER INFORMATION: synthetic sequence

<400> SEQUENCE: 36

Lys Glu Phe Met Arg Phe Lys Val His Met Glu Gly Ser Val Asn Gly
1               5                   10                  15

His Glu Phe Glu Ile Glu Gly Glu Gly Glu Gly Arg Pro Tyr Glu Ala
            20                  25                  30

Phe Gln Thr Ala Lys Leu Lys Val Thr Lys Gly Gly Pro Leu Pro Phe
        35                  40                  45

Ala Trp Asp Ile Leu Ser Pro Gln Phe Met Tyr Gly Ser Lys Ala Tyr
    50                  55                  60

Ile Lys His Pro Ala Asp Ile Pro Asp Tyr Phe Lys Leu Ser Phe Pro
65                  70                  75                  80

Glu Gly Phe Arg Trp Asp Arg Val Met Asn Phe Glu Asp Gly Gly Ile
```

```
                    85                  90                  95
Ile His Val Asn Gln Asp Ser Ser Leu Gln Asp Gly Val Phe Ile Tyr
            100                 105                 110

Lys Val Lys Leu Arg Gly Thr Asn Phe Pro Pro Asp Gly Pro Val Met
            115                 120                 125

Gln Lys Lys Thr Met Gly Trp Glu Ala Thr Arg
        130                 135
```

<210> SEQ ID NO 37
<211> LENGTH: 310
<212> TYPE: PRT
<213> ORGANISM: Artificial sequence
<220> FEATURE:
<223> OTHER INFORMATION: synthetic sequence

<400> SEQUENCE: 37

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
```

```
305                 310
```

<210> SEQ ID NO 38
<211> LENGTH: 340
<212> TYPE: PRT
<213> ORGANISM: Artificial sequence
<220> FEATURE:
<223> OTHER INFORMATION: synthetic sequence

<400> SEQUENCE: 38

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Pro Ala Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340
```

<210> SEQ ID NO 39
<211> LENGTH: 310
<212> TYPE: PRT
<213> ORGANISM: Artificial sequence
<220> FEATURE:
<223> OTHER INFORMATION: synthetic sequence

<400> SEQUENCE: 39

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Ser
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 40
<211> LENGTH: 340
<212> TYPE: PRT
<213> ORGANISM: Artificial sequence
<220> FEATURE:
<223> OTHER INFORMATION: synthetic sequence

<400> SEQUENCE: 40

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
            115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro Ala Ala Lys Ser Arg Ile Thr Ser Glu
305                 310                 315                 320

Gly Glu Tyr Ile Pro Leu Asp Gln Ile Asp Ile Asn Val Phe Cys Tyr
            325                 330                 335

Glu Asn Glu Val
            340

<210> SEQ ID NO 41
<211> LENGTH: 300
<212> TYPE: PRT
<213> ORGANISM: Artificial sequence
<220> FEATURE:
<223> OTHER INFORMATION: synthetic sequence

<400> SEQUENCE: 41

Met Asp Tyr Pro Val Ala Arg Ser Leu Ile Val Arg Tyr Pro Thr Asp
1               5                   10                  15

```
Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 42
<211> LENGTH: 330
<212> TYPE: PRT
<213> ORGANISM: Artificial sequence
<220> FEATURE:
<223> OTHER INFORMATION: synthetic sequence

<400> SEQUENCE: 42

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80
```

Val Ala Leu Ile Glu Met Met Lys Ser Ile Ile Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
            210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp Ala Ala Ala Lys
290                 295                 300

Ser Arg Ile Thr Ser Glu Gly Glu Tyr Ile Pro Leu Asp Gln Ile Asp
305                 310                 315                 320

Ile Asn Val Phe Cys Tyr Glu Asn Glu Val
                325                 330

<210> SEQ ID NO 43
<211> LENGTH: 344
<212> TYPE: PRT
<213> ORGANISM: Artificial sequence
<220> FEATURE:
<223> OTHER INFORMATION: synthetic sequence

<400> SEQUENCE: 43

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
        130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 44
<211> LENGTH: 374
<212> TYPE: PRT
<213> ORGANISM: Artificial sequence
<220> FEATURE:
<223> OTHER INFORMATION: synthetic sequence

<400> SEQUENCE: 44

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ala Ala Ala Lys Ser Arg Ile Thr
            340                 345                 350

Ser Glu Gly Glu Tyr Ile Pro Leu Asp Gln Ile Asp Ile Asn Val Phe
        355                 360                 365

Cys Tyr Glu Asn Glu Val
        370

<210> SEQ ID NO 45
<211> LENGTH: 348
<212> TYPE: PRT
<213> ORGANISM: Artificial sequence
<220> FEATURE:
<223> OTHER INFORMATION: synthetic sequence

<400> SEQUENCE: 45

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

Glu Met Ile Lys Phe Ile Ile Glu Tyr Phe His Glu Phe Asp Glu Pro
        130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Val Tyr Gly Ser Thr Val Gly His
        275                 280                 285

Thr Ile Ile Asp Leu Met Ser Lys Asn Cys Trp Gly Leu Leu Gly His
290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 46
<211> LENGTH: 378
<212> TYPE: PRT
<213> ORGANISM: Artificial sequence
<220> FEATURE:
<223> OTHER INFORMATION: synthetic sequence

<400> SEQUENCE: 46

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
            115                 120                 125

```
Glu Met Ile Lys Phe Ile Ile Glu Tyr Phe His Glu Phe Asp Glu Pro
    130                 135                 140
Ala Val Ile Tyr Ser Ser Asn Gly Asn Lys Thr Val Trp Leu Arg Tyr
145                 150                 155                 160
Ala Glu Trp Leu Leu Thr Cys Pro Val Ile Leu Ile His Leu Ser Asn
                165                 170                 175
Leu Thr Gly Leu Ala Asn Asp Tyr Asn Lys Arg Thr Met Gly Leu Leu
            180                 185                 190
Val Ser Asp Ile Gly Thr Ile Val Trp Gly Thr Thr Ala Ala Leu Ser
        195                 200                 205
Lys Gly Tyr Val Arg Val Ile Phe Phe Leu Met Gly Leu Cys Tyr Gly
210                 215                 220
Ile Tyr Thr Phe Phe Asn Ala Ala Lys Val Tyr Ile Glu Ala Tyr His
225                 230                 235                 240
Thr Val Pro Lys Gly Arg Cys Arg Gln Val Val Thr Gly Met Ala Trp
                245                 250                 255
Leu Phe Phe Val Ser Trp Gly Met Phe Pro Ile Leu Phe Ile Leu Gly
            260                 265                 270
Pro Glu Gly Phe Gly Val Leu Ser Val Tyr Gly Ser Thr Val Gly His
        275                 280                 285
Thr Ile Ile Asp Leu Met Ser Lys Asn Cys Trp Gly Leu Leu Gly His
290                 295                 300
Tyr Leu Arg Val Leu Ile His Glu His Ile Leu Ile His Gly Asp Ile
305                 310                 315                 320
Arg Lys Thr Thr Lys Leu Asn Ile Gly Gly Thr Glu Ile Glu Val Glu
                325                 330                 335
Thr Leu Val Glu Asp Glu Ala Glu Ala Gly Ala Val Ala Ala Ala Lys
            340                 345                 350
Ser Arg Ile Thr Ser Glu Gly Glu Tyr Ile Pro Leu Asp Gln Ile Asp
        355                 360                 365
Ile Asn Val Phe Cys Tyr Glu Asn Glu Val
        370                 375

<210> SEQ ID NO 47
<211> LENGTH: 350
<212> TYPE: PRT
<213> ORGANISM: Artificial sequence
<220> FEATURE:
<223> OTHER INFORMATION: synthetic sequence

<400> SEQUENCE: 47

Met Val Ser Arg Arg Pro Trp Leu Leu Ala Leu Ala Leu Ala Val Ala
1               5                   10                  15
Leu Ala Ala Gly Ser Ala Gly Ala Ser Thr Gly Ser Asp Ala Thr Val
            20                  25                  30
Pro Val Ala Thr Gln Asp Gly Pro Asp Tyr Val Phe His Arg Ala His
        35                  40                  45
Glu Arg Met Leu Phe Gln Thr Ser Tyr Thr Leu Glu Asn Asn Gly Ser
    50                  55                  60
Val Ile Cys Ile Pro Asn Asn Gly Gln Cys Phe Cys Leu Ala Trp Leu
65                  70                  75                  80
Lys Ser Asn Gly Thr Asn Ala Glu Lys Leu Ala Ala Asn Ile Leu Gln
                85                  90                  95
Trp Val Thr Phe Ala Leu Ser Val Ala Cys Leu Gly Trp Tyr Ala Tyr
            100                 105                 110
```

```
Gln Ala Trp Arg Ala Thr Cys Gly Trp Glu Val Tyr Val Ala Leu
            115                 120                 125
Ile Glu Met Met Lys Ser Ile Ile Glu Ala Phe His Glu Phe Asp Ser
130                 135                 140
Pro Ala Thr Leu Trp Leu Ser Ser Gly Asn Gly Val Val Trp Met Arg
145                 150                 155                 160
Tyr Gly Glu Trp Leu Leu Thr Cys Pro Val Ile Leu Ile His Leu Ser
                165                 170                 175
Asn Leu Thr Gly Leu Lys Asp Asp Tyr Ser Lys Arg Thr Met Gly Leu
            180                 185                 190
Leu Val Ser Asp Val Gly Cys Ile Val Trp Gly Ala Thr Ser Ala Met
        195                 200                 205
Cys Thr Gly Trp Thr Lys Ile Leu Phe Phe Leu Ile Ser Leu Ser Tyr
210                 215                 220
Gly Met Tyr Thr Tyr Phe His Ala Ala Lys Val Tyr Ile Glu Ala Phe
225                 230                 235                 240
His Thr Val Pro Lys Gly Leu Cys Arg Gln Leu Val Arg Ala Met Ala
                245                 250                 255
Trp Leu Phe Phe Val Ser Trp Gly Met Phe Pro Val Leu Phe Leu Leu
            260                 265                 270
Gly Pro Glu Gly Phe Gly His Ile Ser Pro Tyr Gly Ser Ala Ile Gly
        275                 280                 285
His Ser Ile Leu Asp Leu Ile Ala Lys Asn Met Trp Gly Val Leu Gly
290                 295                 300
Asn Tyr Leu Arg Val Lys Ile His Glu His Ile Leu Leu Tyr Gly Asp
305                 310                 315                 320
Ile Arg Lys Lys Gln Lys Ile Thr Ile Ala Gly Gln Glu Met Glu Val
                325                 330                 335
Glu Thr Leu Val Ala Glu Glu Glu Asp Lys Tyr Glu Ser Ser
            340                 345                 350

<210> SEQ ID NO 48
<211> LENGTH: 380
<212> TYPE: PRT
<213> ORGANISM: Artificial sequence
<220> FEATURE:
<223> OTHER INFORMATION: synthetic sequence

<400> SEQUENCE: 48

Met Val Ser Arg Arg Pro Trp Leu Leu Ala Leu Ala Leu Ala Val Ala
1               5                   10                  15
Leu Ala Ala Gly Ser Ala Gly Ala Ser Thr Gly Ser Asp Ala Thr Val
            20                  25                  30
Pro Val Ala Thr Gln Asp Gly Pro Asp Tyr Val Phe His Arg Ala His
        35                  40                  45
Glu Arg Met Leu Phe Gln Thr Ser Tyr Thr Leu Glu Asn Asn Gly Ser
    50                  55                  60
Val Ile Cys Ile Pro Asn Asn Gly Gln Cys Phe Cys Leu Ala Trp Leu
65                  70                  75                  80
Lys Ser Asn Gly Thr Asn Ala Glu Lys Leu Ala Ala Asn Ile Leu Gln
                85                  90                  95
Trp Val Thr Phe Ala Leu Ser Val Ala Cys Leu Gly Trp Tyr Ala Tyr
            100                 105                 110
Gln Ala Trp Arg Ala Thr Cys Gly Trp Glu Glu Val Tyr Val Ala Leu
        115                 120                 125
```

Ile Glu Met Met Lys Ser Ile Ile Glu Ala Phe His Glu Phe Asp Ser
130                 135                 140

Pro Ala Thr Leu Trp Leu Ser Ser Gly Asn Gly Val Val Trp Met Arg
145                 150                 155                 160

Tyr Gly Glu Trp Leu Leu Thr Cys Pro Val Ile Leu Ile His Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Pro Tyr Gly Ser Ala Ile Gly
        275                 280                 285

His Ser Ile Leu Asp Leu Ile Ala Lys Asn Met Trp Gly Val Leu Gly
290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
            340                 345                 350

Ala Lys Ser Arg Ile Thr Ser Glu Gly Glu Tyr Ile Pro Leu Asp Gln
        355                 360                 365

Ile Asp Ile Asn Val Phe Cys Tyr Glu Asn Glu Val
370                 375                 380

<210> SEQ ID NO 49
<211> LENGTH: 316
<212> TYPE: PRT
<213> ORGANISM: Artificial sequence
<220> FEATURE:
<223> OTHER INFORMATION: synthetic sequence

<400> SEQUENCE: 49

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Val Tyr Val
            85                  90                  95

Cys Ser Val Glu Leu Ile Lys Val Ile Leu Glu Ile Tyr Phe Glu Phe
                100                 105                 110

Thr Ser Pro Ala Met Leu Phe Leu Tyr Gly Gly Asn Ile Thr Pro Trp
            115                 120                 125

Leu Arg Tyr Ala Glu Trp Leu Leu Thr Cys Pro Val Ile Leu Ile His
        130                 135                 140

Leu Ser Asn Ile Thr Gly Leu Ser Glu Glu Tyr Asn Lys Arg Thr Met
145                 150                 155                 160

Ala Leu Leu Val Ser Asp Leu Gly Thr Ile Cys Met Gly Val Thr Ala
                165                 170                 175

Ala Leu Ala Thr Gly Trp Val Lys Trp Leu Phe Tyr Cys Ile Gly Leu
            180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
    210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
                245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
    290                 295                 300

Asp Val Leu Ala Phe Val Thr Glu Glu Asp Lys Val
305                 310                 315

<210> SEQ ID NO 50
<211> LENGTH: 346
<212> TYPE: PRT
<213> ORGANISM: Artificial sequence
<220> FEATURE:
<223> OTHER INFORMATION: synthetic sequence

<400> SEQUENCE: 50

Met Gly Gly Ala Pro Ala Pro Asp Ala His Ser Ala Pro Pro Gly Asn
1               5                   10                  15

Asp Ser Ala Gly Gly Ser Glu Tyr His Ala Pro Ala Gly Tyr Gln Val
            20                  25                  30

Asn Pro Pro Tyr His Pro Val His Gly Tyr Glu Glu Gln Cys Ser Ser
        35                  40                  45

Ile Tyr Ile Tyr Tyr Gly Ala Leu Trp Glu Gln Thr Ala Arg Gly
    50                  55                  60

Phe Gln Trp Phe Ala Val Phe Leu Ser Ala Leu Phe Leu Ala Phe Tyr
65                  70                  75                  80

Gly Trp His Ala Tyr Lys Ala Ser Val Gly Trp Glu Glu Val Tyr Val
                85                  90                  95

Cys Ser Val Glu Leu Ile Lys Val Ile Leu Glu Ile Tyr Phe Glu Phe
            100                 105                 110

Thr Ser Pro Ala Met Leu Phe Leu Tyr Gly Gly Asn Ile Thr Pro Trp
        115                 120                 125

Leu Arg Tyr Ala Glu Trp Leu Leu Thr Cys Pro Val Ile Leu Ile His
    130                 135                 140

Leu Ser Asn Ile Thr Gly Leu Ser Glu Glu Tyr Asn Lys Arg Thr Met
145                 150                 155                 160

```
Ala Leu Leu Val Ser Asp Leu Gly Thr Ile Cys Met Gly Val Thr Ala
            165                 170                 175

Ala Leu Ala Thr Gly Trp Val Lys Trp Leu Phe Tyr Cys Ile Gly Leu
        180                 185                 190

Val Tyr Gly Thr Gln Thr Phe Tyr Asn Ala Gly Ile Ile Tyr Val Glu
        195                 200                 205

Ser Tyr Tyr Ile Met Pro Ala Gly Gly Cys Lys Lys Leu Val Leu Ala
        210                 215                 220

Met Thr Ala Val Tyr Tyr Ser Ser Trp Leu Met Phe Pro Gly Leu Phe
225                 230                 235                 240

Ile Phe Gly Pro Glu Gly Met His Thr Leu Ser Val Ala Gly Ser Thr
            245                 250                 255

Ile Gly His Thr Ile Ala Asp Leu Leu Ser Lys Asn Ile Trp Gly Leu
            260                 265                 270

Leu Gly His Phe Leu Arg Ile Lys Ile His Glu His Ile Ile Met Tyr
        275                 280                 285

Gly Asp Ile Arg Arg Pro Val Ser Ser Gln Phe Leu Gly Arg Lys Val
        290                 295                 300

Asp Val Leu Ala Phe Val Thr Glu Asp Lys Val Ala Ala Ala Lys
305                 310                 315                 320

Ser Arg Ile Thr Ser Glu Gly Glu Tyr Ile Pro Leu Asp Gln Ile Asp
            325                 330                 335

Ile Asn Val Phe Cys Tyr Glu Asn Glu Val
            340                 345

<210> SEQ ID NO 51
<211> LENGTH: 350
<212> TYPE: PRT
<213> ORGANISM: Artificial sequence
<220> FEATURE:
<223> OTHER INFORMATION: synthetic sequence

<400> SEQUENCE: 51

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Gly Val Tyr Val
        115                 120                 125

Cys Cys Val Glu Val Leu Phe Val Thr Leu Glu Ile Phe Lys Glu Phe
    130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175
```

```
Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
        210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ala Lys Glu Phe Trp Thr Phe
        290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
                325                 330                 335

Glu Val Glu Glu Phe Val Glu Glu Asp Glu Asp Thr Val
            340                 345                 350

<210> SEQ ID NO 52
<211> LENGTH: 380
<212> TYPE: PRT
<213> ORGANISM: Artificial sequence
<220> FEATURE:
<223> OTHER INFORMATION: synthetic sequence

<400> SEQUENCE: 52

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
        130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190
```

```
Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
            245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
            275                 280                 285

Ile Gly His Ser Ile Cys Asp Ile Ile Ala Lys Glu Phe Trp Thr Phe
            290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Glu Asp Glu Asp Thr Val Ala Ala
            340                 345                 350

Ala Lys Ser Arg Ile Thr Ser Glu Gly Glu Tyr Ile Pro Leu Asp Gln
            355                 360                 365

Ile Asp Ile Asn Val Phe Cys Tyr Glu Asn Glu Val
370                 375                 380

<210> SEQ ID NO 53
<211> LENGTH: 345
<212> TYPE: PRT
<213> ORGANISM: Artificial sequence
<220> FEATURE:
<223> OTHER INFORMATION: synthetic sequence

<400> SEQUENCE: 53

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
            85                  90                  95

Phe Ser Ile Ala Ile Ala Leu Leu Thr Phe Tyr Gly Phe Ser Ala Trp
                100                 105                 110

Lys Ala Thr Cys Gly Trp Glu Glu Val Tyr Val Cys Cys Val Glu Val
            115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175
```

```
Gly Leu Lys Asn Asp Tyr Ser Lys Arg Thr Met Gly Leu Ile Val Ser
                180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
    210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
    275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Phe
                325                 330                 335

Val Glu Glu Glu Asp Glu Asp Thr Val
            340                 345

<210> SEQ ID NO 54
<211> LENGTH: 375
<212> TYPE: PRT
<213> ORGANISM: Artificial sequence
<220> FEATURE:
<223> OTHER INFORMATION: synthetic sequence

<400> SEQUENCE: 54

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Val Glu Val
    115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190
```

```
Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
        210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
    290                 295                 300

Arg Ile Lys Ile His Glu His Ile Leu Ile His Gly Asp Ile Arg Lys
305                 310                 315                 320

Thr Thr Lys Met Glu Ile Gly Gly Glu Val Glu Val Glu Glu Phe
                325                 330                 335

Val Glu Glu Glu Asp Glu Asp Thr Val Ala Ala Ala Lys Ser Arg Ile
            340                 345                 350

Thr Ser Glu Gly Glu Tyr Ile Pro Leu Asp Gln Ile Asp Ile Asn Val
        355                 360                 365

Phe Cys Tyr Glu Asn Glu Val
    370                 375

<210> SEQ ID NO 55
<211> LENGTH: 325
<212> TYPE: PRT
<213> ORGANISM: Artificial sequence
<220> FEATURE:
<223> OTHER INFORMATION: synthetic sequence

<400> SEQUENCE: 55

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175
```

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
            195                 200                 205

Ile Ala Lys Val Tyr Ile Glu Ser Tyr His Thr Leu Pro Lys Gly Val
            210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
            245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
            275                 280                 285

His Glu His Ile Leu Ile His Gly Asp Ile Arg Lys Thr Thr Thr Ile
            290                 295                 300

Asn Val Ala Gly Glu Asn Met Glu Ile Glu Thr Phe Val Asp Glu Glu
305                 310                 315                 320

Glu Glu Gly Gly Val
            325

<210> SEQ ID NO 56
<211> LENGTH: 355
<212> TYPE: PRT
<213> ORGANISM: Artificial sequence
<220> FEATURE:
<223> OTHER INFORMATION: synthetic sequence

<400> SEQUENCE: 56

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
                20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
        50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
            195                 200                 205

```
Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
                260                 265                 270

Ser Lys Asn Thr Trp Gly Phe Leu Gly His His Leu Arg Val Lys Ile
            275                 280                 285

His Glu His Ile Leu Ile His Gly Asp Ile Arg Lys Thr Thr Thr Ile
290                 295                 300

Asn Val Ala Gly Glu Asn Met Glu Ile Glu Thr Phe Val Asp Glu Glu
305                 310                 315                 320

Glu Glu Gly Gly Val Ala Ala Lys Ser Arg Ile Thr Ser Glu Gly
                325                 330                 335

Glu Tyr Ile Pro Leu Asp Gln Ile Asp Ile Asn Val Phe Cys Tyr Glu
                340                 345                 350

Asn Glu Val
        355
```

<210> SEQ ID NO 57
<211> LENGTH: 258
<212> TYPE: PRT
<213> ORGANISM: Artificial sequence
<220> FEATURE:
<223> OTHER INFORMATION: synthetic sequence

<400> SEQUENCE: 57

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Gly Thr Glu Gly Ala Gly Val
        195                 200                 205
```

```
Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 58
<211> LENGTH: 293
<212> TYPE: PRT
<213> ORGANISM: Artificial sequence
<220> FEATURE:
<223> OTHER INFORMATION: synthetic sequence

<400> SEQUENCE: 58

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Ala Ala Lys Ser Arg Ile Thr Ser
            260                 265                 270

Glu Gly Glu Tyr Ile Pro Leu Asp Gln Ile Asp Ile Asn Val Phe Cys
        275                 280                 285

Tyr Glu Asn Glu Val
    290
```

```
<210> SEQ ID NO 59
<211> LENGTH: 248
<212> TYPE: PRT
<213> ORGANISM: Artificial sequence
<220> FEATURE:
<223> OTHER INFORMATION: synthetic sequence

<400> SEQUENCE: 59

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro
                245

<210> SEQ ID NO 60
<211> LENGTH: 278
<212> TYPE: PRT
<213> ORGANISM: Artificial sequence
<220> FEATURE:
<223> OTHER INFORMATION: synthetic sequence

<400> SEQUENCE: 60

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60
```

```
Ala Ala Tyr Leu Ser Met Phe Phe Gly Ile Gly Leu Thr Glu Val Thr
 65                  70                  75                  80

Val Ala Gly Glu Val Leu Asp Ile Tyr Tyr Ala Arg Tyr Ala Asp Trp
             85                  90                  95

Leu Phe Thr Thr Pro Leu Leu Leu Asp Leu Ala Leu Leu Ala Lys
            100                 105                 110

Val Asp Arg Val Ser Ile Gly Thr Leu Val Gly Val Asp Ala Leu Met
        115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Leu Tyr
145                 150                 155                 160

Phe Leu Ala Thr Ser Leu Arg Ala Ala Ala Lys Glu Arg Gly Pro Glu
            165                 170                 175

Val Ala Ser Thr Phe Asn Thr Leu Thr Ala Leu Val Leu Val Leu Trp
        180                 185                 190

Thr Ala Tyr Pro Ile Leu Trp Ile Ile Gly Thr Glu Gly Ala Gly Val
    195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ala Ala Lys Ser Arg Ile Thr
            245                 250                 255

Ser Glu Gly Glu Tyr Ile Pro Leu Asp Gln Ile Asp Ile Asn Val Phe
        260                 265                 270

Cys Tyr Glu Asn Glu Val
        275

<210> SEQ ID NO 61
<211> LENGTH: 242
<212> TYPE: PRT
<213> ORGANISM: Artificial sequence
<220> FEATURE:
<223> OTHER INFORMATION: synthetic sequence

<400> SEQUENCE: 61

Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
            20                  25                  30

Ile Val Phe Ala Cys Ile Thr Leu Leu Gly Ile Asn Ala Ala Lys
        35                  40                  45

Ser Lys Ala Ala Ser Arg Val Leu Phe Pro Ala Thr Phe Val Thr Gly
    50                  55                  60

Ile Ala Ser Ile Ala Tyr Phe Ser Met Ala Ser Gly Gly Trp Val
65                  70                  75                  80

Ile Ala Pro Asp Cys Arg Gln Leu Phe Val Ala Arg Tyr Leu Asp Trp
            85                  90                  95

Leu Ile Thr Thr Pro Leu Leu Leu Ile Asp Leu Gly Leu Val Ala Gly
            100                 105                 110

Val Ser Arg Trp Asp Ile Met Ala Leu Cys Leu Ser Asp Val Leu Met
        115                 120                 125

Ile Ala Thr Gly Ala Phe Gly Ser Leu Thr Val Gly Asn Val Lys Trp
    130                 135                 140
```

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
            165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
            195                 200                 205

Val Thr Phe Glu Val Leu Ile Tyr Gly Val Leu Asp Val Ile Ser Lys
            210                 215                 220

Ala Val Phe Gly Leu Ile Leu Met Ser Gly Ala Ala Thr Gly Tyr Glu
225                 230                 235                 240

Ser Ile

<210> SEQ ID NO 62
<211> LENGTH: 272
<212> TYPE: PRT
<213> ORGANISM: Artificial sequence
<220> FEATURE:
<223> OTHER INFORMATION: synthetic sequence

<400> SEQUENCE: 62

Met Leu Val Gly Glu Gly Ala Lys Leu Asp Val His Gly Cys Lys Thr
1               5                   10                  15

Val Asp Met Ala Ser Ser Phe Gly Lys Ala Leu Leu Glu Phe Val Phe
            20                  25                  30

Ile Val Phe Ala Cys Ile Thr Leu Leu Gly Ile Asn Ala Ala Lys
            35                  40                  45

Ser Lys Ala Ala Ser Arg Val Leu Phe Pro Ala Thr Phe Val Thr Gly
50                  55                  60

Ile Ala Ser Ile Ala Tyr Phe Ser Met Ala Ser Gly Gly Gly Trp Val
65                  70                  75                  80

Ile Ala Pro Asp Cys Arg Gln Leu Phe Val Ala Arg Tyr Leu Asp Trp
            85                  90                  95

Leu Ile Thr Thr Pro Leu Leu Leu Ile Asp Leu Gly Leu Val Ala Gly
            100                 105                 110

Val Ser Arg Trp Asp Ile Met Ala Leu Cys Leu Ser Asp Val Leu Met
            115                 120                 125

Ile Ala Thr Gly Ala Phe Gly Ser Leu Thr Val Gly Asn Val Lys Trp
130                 135                 140

Val Trp Trp Phe Phe Gly Met Cys Trp Phe Leu His Ile Ile Phe Ala
145                 150                 155                 160

Leu Gly Lys Ser Trp Ala Glu Ala Ala Lys Ala Lys Gly Gly Asp Ser
            165                 170                 175

Ala Ser Val Tyr Ser Lys Ile Ala Gly Ile Thr Val Ile Thr Trp Phe
            180                 185                 190

Cys Tyr Pro Val Val Trp Val Phe Ala Glu Gly Phe Gly Asn Phe Ser
            195                 200                 205

Val Thr Phe Glu Val Leu Ile Tyr Gly Val Leu Asp Val Ile Ser Lys
            210                 215                 220

Ala Val Phe Gly Leu Ile Leu Met Ser Gly Ala Ala Thr Gly Tyr Glu
225                 230                 235                 240

Ser Ile Ala Ala Ala Lys Ser Arg Ile Thr Ser Glu Gly Glu Tyr Ile
            245                 250                 255

Pro Leu Asp Gln Ile Asp Ile Asn Val Phe Cys Tyr Glu Asn Glu Val

<210> SEQ ID NO 63
<211> LENGTH: 262
<212> TYPE: PRT
<213> ORGANISM: Artificial sequence
<220> FEATURE:
<223> OTHER INFORMATION: synthetic sequence

<400> SEQUENCE: 63

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Phe Asn Val Gly Leu Gly Val
65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
        115                 120                 125

Trp Thr Leu Gly Ile Ala Ser Ala Val Met Val Ala Leu Gly Tyr Pro
    130                 135                 140

Gly Glu Ile Gln Asp Asp Leu Ser Val Arg Trp Phe Trp Ala Cys
145                 150                 155                 160

Ala Met Val Pro Phe Val Tyr Val Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
        195                 200                 205

Tyr Ile Val Lys Asn Ile Gly Leu Ala Gly Ser Thr Ala Thr Met Tyr
    210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
            260

<210> SEQ ID NO 64
<211> LENGTH: 292
<212> TYPE: PRT
<213> ORGANISM: Artificial sequence
<220> FEATURE:
<223> OTHER INFORMATION: synthetic sequence

<400> SEQUENCE: 64

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

```
Phe Phe Trp Leu Gln Leu Pro Asn Val Thr Lys Asn Tyr Arg Thr Ala
            35                  40                  45

Leu Thr Ile Thr Gly Ile Val Thr Leu Ile Ala Thr Tyr His Tyr Phe
 50                  55                  60

Arg Ile Phe Asn Ser Trp Val Ala Ala Phe Asn Val Gly Leu Gly Val
 65                  70                  75                  80

Asn Gly Ala Tyr Glu Val Thr Val Ser Gly Thr Pro Phe Asn Asp Ala
                85                  90                  95

Tyr Arg Tyr Val Asp Trp Leu Leu Thr Val Pro Leu Leu Leu Val Glu
            100                 105                 110

Leu Ile Leu Val Met Lys Leu Pro Ala Lys Glu Thr Val Cys Leu Ala
            115                 120                 125

Trp Thr Leu Gly Ile Ala Ser Ala Val Met Val Ala Leu Gly Tyr Pro
130                 135                 140

Gly Glu Ile Gln Asp Asp Leu Ser Val Arg Trp Phe Trp Trp Ala Cys
145                 150                 155                 160

Ala Met Val Pro Phe Val Tyr Val Gly Thr Leu Val Val Gly Leu
                165                 170                 175

Gly Ala Ala Thr Ala Lys Gln Pro Glu Gly Val Val Asp Leu Val Ser
            180                 185                 190

Ala Ala Arg Tyr Leu Thr Val Val Ser Trp Leu Thr Tyr Pro Phe Val
            195                 200                 205

Tyr Ile Val Lys Asn Ile Gly Leu Ala Gly Ser Thr Ala Met Tyr
            210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala Ala Ala Lys Ser Arg Ile Thr Ser Glu
            260                 265                 270

Gly Glu Tyr Ile Pro Leu Asp Gln Ile Asp Ile Asn Val Phe Cys Tyr
            275                 280                 285

Glu Asn Glu Val
    290

<210> SEQ ID NO 65
<211> LENGTH: 313
<212> TYPE: PRT
<213> ORGANISM: Artificial sequence
<220> FEATURE:
<223> OTHER INFORMATION: synthetic sequence

<400> SEQUENCE: 65

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
            35                  40                  45

Asp Ser Gly Ser Lys Thr Leu Trp Val Phe Val Leu Met Leu Ile
 50                  55                  60

Ala Ser Ala Ala Phe Thr Ala Leu Ser Trp Lys Ile Pro Val Asn Arg
 65                  70                  75                  80

Arg Leu Tyr His Val Ile Thr Thr Ile Thr Leu Thr Ala Ala Leu
                85                  90                  95
```

```
Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
            260                 265                 270

Phe Gly Ala Trp Leu Leu Val Thr His Ala Asn Leu Arg Glu Ser Asp
        275                 280                 285

Val Glu Leu Asn Gly Phe Trp Ala Asn Gly Leu Asn Arg Glu Gly Ala
    290                 295                 300

Ile Arg Ile Gly Glu Asp Asp Gly Ala
305                 310

<210> SEQ ID NO 66
<211> LENGTH: 351
<212> TYPE: PRT
<213> ORGANISM: Artificial sequence
<220> FEATURE:
<223> OTHER INFORMATION: synthetic sequence

<400> SEQUENCE: 66

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Val Phe Val Leu Met Leu Ile
50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Ile Thr Leu Thr Ala Ala Leu
                85                  90                  95

Ser Tyr Phe Ala Met Ala Thr Gly His Gly Val Ala Leu Asn Lys Ile
            100                 105                 110

Val Ile Arg Thr Gln His Asp His Val Pro Asp Thr Tyr Glu Thr Val
        115                 120                 125

Tyr Arg Gln Val Tyr Tyr Ala Arg Tyr Ile Asp Trp Ala Ile Thr Thr
    130                 135                 140
```

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
            180                 185                 190

Tyr Thr Ile Ala Cys Ile Ala Tyr Ile Phe Val Val Trp His Leu Val
        195                 200                 205

Leu Asn Gly Gly Ala Asn Ala Arg Val Lys Gly Glu Lys Leu Arg Ser
    210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
                260                 265                 270

Phe Gly Ala Trp Leu Leu Val Thr His Ala Asn Leu Arg Glu Ser Asp
            275                 280                 285

Val Glu Leu Asn Gly Phe Trp Ala Asn Gly Leu Asn Arg Glu Gly Ala
        290                 295                 300

Ile Arg Ile Gly Glu Asp Asp Gly Ala Arg Pro Val Ala Val Ser
305                 310                 315                 320

Lys Ala Ala Ala Lys Ser Arg Ile Thr Ser Glu Gly Glu Tyr Ile Pro
                325                 330                 335

Leu Asp Gln Ile Asp Ile Asn Val Phe Cys Tyr Glu Asn Glu Val
            340                 345                 350

<210> SEQ ID NO 67
<211> LENGTH: 291
<212> TYPE: PRT
<213> ORGANISM: Artificial sequence
<220> FEATURE:
<223> OTHER INFORMATION: synthetic sequence

<400> SEQUENCE: 67

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

-continued

```
Val Thr Gly Leu Ala Ala Leu Thr Thr Ser Ser His Leu Met Arg
            165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Val Met Trp Leu Gly
            210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
            245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
            275                 280                 285

Ala Asp Asp
            290

<210> SEQ ID NO 68
<211> LENGTH: 320
<212> TYPE: PRT
<213> ORGANISM: Artificial sequence
<220> FEATURE:
<223> OTHER INFORMATION: synthetic sequence

<400> SEQUENCE: 68

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
        50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
            85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
            115                 120                 125

Leu Ser Thr Pro Met Ile Leu Leu Ala Leu Gly Leu Leu Ala Gly Ser
            130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
            165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Val Met Trp Leu Gly
            210                 215                 220
```

```
Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
            245                 250                 255

Tyr Ile Phe Ala Phe Leu Leu Asn Tyr Leu Thr Ser Asn Glu Ser
        260                 265                 270

Val Val Ser Gly Ser Ile Leu Asp Val Pro Ser Ala Ser Gly Thr Pro
        275                 280                 285

Ala Asp Asp Ala Ala Lys Ser Arg Ile Thr Ser Glu Gly Glu Tyr
    290                 295                 300

Ile Pro Leu Asp Gln Ile Asp Ile Asn Phe Cys Tyr Glu Asn Glu Val
305                 310                 315                 320
```

<210> SEQ ID NO 69
<211> LENGTH: 303
<212> TYPE: PRT
<213> ORGANISM: Artificial sequence
<220> FEATURE:
<223> OTHER INFORMATION: synthetic sequence

<400> SEQUENCE: 69

```
Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
        35                  40                  45

Leu Ile Ala Val Ser Thr Ile Leu Val Pro Val Val Ser Ile Ala Ser
    50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
                85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Ala Gly Ser Asn
        115                 120                 125

Ala Thr Lys Leu Phe Thr Ala Ile Thr Phe Asp Ile Ala Met Cys Val
130                 135                 140

Thr Gly Leu Ala Ala Ala Leu Thr Thr Ser Ser His Leu Met Arg Trp
145                 150                 155                 160

Phe Trp Tyr Ala Ile Ser Cys Ala Cys Phe Leu Val Val Leu Tyr Ile
                165                 170                 175

Leu Leu Val Glu Trp Ala Gln Asp Ala Lys Ala Ala Gly Thr Ala Asp
            180                 185                 190

Met Phe Asn Thr Leu Lys Leu Leu Thr Val Val Met Trp Leu Gly Tyr
        195                 200                 205

Pro Ile Val Trp Ala Leu Gly Val Glu Gly Ile Ala Val Leu Pro Val
    210                 215                 220

Gly Val Thr Ser Trp Gly Tyr Ser Phe Leu Asp Ile Val Ala Lys Tyr
225                 230                 235                 240

Ile Phe Ala Phe Leu Leu Leu Asn Tyr Leu Thr Ser Asn Glu Ser Val
                245                 250                 255

Val Ser Gly Ser Ile Leu Asp Val Pro Ser Ala Ser Gly Thr Pro Ala
            260                 265                 270
```

-continued

Asp Asp Ala Ala Ala Lys Ser Arg Ile Thr Ser Glu Gly Glu Tyr Ile
              275                 280                 285

Pro Leu Asp Gln Ile Asp Ile Asn Phe Cys Tyr Glu Asn Glu Val
          290                 295                 300

<210> SEQ ID NO 70
<211> LENGTH: 365
<212> TYPE: PRT
<213> ORGANISM: Artificial sequence
<220> FEATURE:
<223> OTHER INFORMATION: synthetic sequence

<400> SEQUENCE: 70

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
    130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285

Gly Arg Glu Gly Phe Gly His Ile Thr Tyr Phe Gly Ser Ser Ile Gly
    290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile Ile His Gly Asn
                325                 330                 335

```
Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val
        355                 360                 365

<210> SEQ ID NO 71
<211> LENGTH: 395
<212> TYPE: PRT
<213> ORGANISM: Artificial sequence
<220> FEATURE:
<223> OTHER INFORMATION: synthetic sequence

<400> SEQUENCE: 71

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
            20                  25                  30

Glu Arg Arg Pro Pro Ser Glu Arg Asn Thr Pro Tyr Ala Asn Ile Lys
        35                  40                  45

Lys Val Pro Asn Ile Thr Glu Pro Asn Ala Asn Val Gln Leu Asp Gly
    50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
            115                 120                 125

Ala Trp Lys Ala Thr Val Gly Trp Glu Glu Val Tyr Val Asn Ile Ile
        130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285

Gly Arg Glu Gly Phe Gly His Ile Thr Tyr Phe Gly Ser Ser Ile Gly
    290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile Ile His Gly Asn
                325                 330                 335
```

Leu Thr Lys Lys Asn Lys Ile Asn Ile Ala Gly Asp Asn Val Glu Val
            340                 345                 350

Glu Glu Tyr Val Asp Ser Asn Asp Lys Asp Ser Asp Val Ala Ala Ala
        355                 360                 365

Lys Ser Arg Ile Thr Ser Glu Gly Glu Tyr Ile Pro Leu Asp Gln Ile
    370                 375                 380

Asp Ile Asn Val Phe Cys Tyr Glu Asn Glu Val
385                 390                 395

<210> SEQ ID NO 72
<211> LENGTH: 348
<212> TYPE: PRT
<213> ORGANISM: Artificial sequence
<220> FEATURE:
<223> OTHER INFORMATION: synthetic sequence

<400> SEQUENCE: 72

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

Thr Ile Ile Asp Leu Met Ser Lys Gln Cys Trp Gly Leu Leu Gly His
    290                 295                 300

```
Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 73
<211> LENGTH: 378
<212> TYPE: PRT
<213> ORGANISM: Artificial sequence
<220> FEATURE:
<223> OTHER INFORMATION: synthetic sequence

<400> SEQUENCE: 73

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Ile Leu Ile Arg Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Lys Tyr Gly Ser Asn Val Gly His
            275                 280                 285

Thr Ile Ile Asp Leu Met Ser Lys Gln Cys Trp Gly Leu Leu Gly His
    290                 295                 300

Tyr Leu Arg Val Leu Ile His Glu His Ile Leu Ile His Gly Asp Ile
305                 310                 315                 320
```

Arg Lys Thr Thr Lys Leu Asn Ile Gly Gly Thr Glu Ile Glu Val Glu
            325                 330                 335

Thr Leu Val Glu Asp Glu Ala Glu Ala Gly Ala Val Ala Ala Ala Lys
        340                 345                 350

Ser Arg Ile Thr Ser Glu Gly Glu Tyr Ile Pro Leu Asp Gln Ile Asp
            355                 360                 365

Ile Asn Val Phe Cys Tyr Glu Asn Glu Val
370                 375

<210> SEQ ID NO 74
<211> LENGTH: 348
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (167)..(167)
<223> OTHER INFORMATION: Xaa can be any naturally occurring amino acid

<400> SEQUENCE: 74

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
            260                 265                 270

Pro Glu Gly Phe Gly Val Leu Ser Lys Tyr Gly Ser Asn Val Gly His
        275                 280                 285

```
Thr Ile Ile Asp Leu Met Ser Lys Gln Cys Trp Gly Leu Gly His
        290                 295                 300

Tyr Leu Arg Val Leu Ile His Glu His Ile Leu Ile His Gly Asp Ile
305                 310                 315                 320

Arg Lys Thr Thr Lys Leu Asn Ile Gly Gly Thr Glu Ile Glu Val Glu
                325                 330                 335

Thr Leu Val Glu Asp Glu Ala Glu Ala Gly Ala Val
            340                 345

<210> SEQ ID NO 75
<211> LENGTH: 378
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (167)..(167)
<223> OTHER INFORMATION: Xaa can be any naturally occurring amino acid

<400> SEQUENCE: 75

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
                100                 105                 110

Thr Trp Lys Ser Thr Cys Gly Trp Glu Glu Ile Tyr Val Ala Thr Ile
            115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Xaa Pro Val Ile Leu Ile Arg Leu Ser Asn
                165                 170                 175

Leu Thr Gly Leu Ala Asn Asp Tyr Asn Lys Arg Thr Met Gly Leu Leu
                180                 185                 190

Val Ser Asp Ile Gly Thr Ile Val Trp Gly Thr Thr Ala Ala Leu Ser
            195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Arg Cys Arg Gln Val Val Thr Gly Met Ala Trp
                245                 250                 255

Leu Phe Phe Val Ser Trp Gly Met Phe Pro Ile Leu Phe Ile Leu Gly
                260                 265                 270

Pro Glu Gly Phe Gly Val Leu Ser Lys Tyr Gly Ser Asn Val Gly His
```

```
                275                 280                 285
Thr Ile Ile Asp Leu Met Ser Lys Gln Cys Trp Gly Leu Leu Gly His
    290                 295                 300
Tyr Leu Arg Val Leu Ile His Glu His Ile Leu Ile His Gly Asp Ile
305                 310                 315                 320
Arg Lys Thr Thr Lys Leu Asn Ile Gly Gly Thr Glu Ile Glu Val Glu
                325                 330                 335
Thr Leu Val Glu Asp Glu Ala Glu Ala Gly Ala Val Ala Ala Ala Lys
            340                 345                 350
Ser Arg Ile Thr Ser Glu Gly Glu Tyr Ile Pro Leu Asp Gln Ile Asp
                355                 360                 365
Ile Asn Val Phe Cys Tyr Glu Asn Glu Val
            370                 375

<210> SEQ ID NO 76
<211> LENGTH: 309
<212> TYPE: PRT
<213> ORGANISM: Artificial sequence
<220> FEATURE:
<223> OTHER INFORMATION: synthetic sequence

<400> SEQUENCE: 76

Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
                20                  25                  30
Gln Cys Phe Cys Leu Ala Trp Leu Lys Ser Asn Gly Thr Asn Ala Glu
            35                  40                  45
Lys Leu Ala Ala Asn Ile Leu Gln Trp Ile Ser Phe Ala Leu Ser Ala
    50                  55                  60
Leu Cys Leu Met Phe Tyr Gly Tyr Gln Thr Trp Lys Ser Thr Cys Gly
65                  70                  75                  80
Trp Glu Glu Ile Tyr Val Ala Thr Ile Ser Met Ile Lys Phe Ile Ile
                85                  90                  95
Glu Tyr Phe His Ser Phe Asp Glu Pro Ala Val Ile Tyr Ser Ser Asn
                100                 105                 110
Gly Asn Lys Thr Lys Trp Leu Arg Tyr Ala Ser Trp Leu Leu Thr Cys
            115                 120                 125
Pro Val Ile Leu Ile Arg Leu Ser Asn Leu Thr Gly Leu Ala Asn Asp
    130                 135                 140
Tyr Asn Lys Arg Thr Met Gly Leu Leu Val Ser Asp Ile Gly Thr Ile
145                 150                 155                 160
Val Trp Gly Thr Thr Ala Ala Leu Ser Lys Gly Tyr Val Arg Val Ile
                165                 170                 175
Phe Phe Leu Met Gly Leu Cys Tyr Gly Ile Tyr Thr Phe Phe Asn Ala
                180                 185                 190
Ala Lys Val Tyr Ile Glu Ala Tyr His Thr Val Pro Lys Gly Arg Cys
            195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Lys Tyr Gly Ser Asn Val Gly His Thr Ile Ile Asp Leu Met Ser
                245                 250                 255
Lys Gln Cys Trp Gly Leu Leu Gly His Tyr Leu Arg Val Leu Ile His
```

```
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
            290                 295                 300
Glu Ala Gly Ala Val
305

<210> SEQ ID NO 77
<211> LENGTH: 339
<212> TYPE: PRT
<213> ORGANISM: Artificial sequence
<220> FEATURE:
<223> OTHER INFORMATION: synthetic sequence

<400> SEQUENCE: 77

Met Asp Tyr Gly Gly Ala Leu Ser Ala Val Gly Leu Phe Gln Thr Ser
1               5                   10                  15
Tyr Thr Leu Glu Asn Asn Gly Ser Val Ile Cys Ile Pro Asn Asn Gly
            20                  25                  30
Gln Cys Phe Cys Leu Ala Trp Leu Lys Ser Asn Gly Thr Asn Ala Glu
        35                  40                  45
Lys Leu Ala Ala Asn Ile Leu Gln Trp Ile Ser Phe Ala Leu Ser Ala
    50                  55                  60
Leu Cys Leu Met Phe Tyr Gly Tyr Gln Thr Trp Lys Ser Thr Cys Gly
65                  70                  75                  80
Trp Glu Glu Ile Tyr Val Ala Thr Ile Ser Met Ile Lys Phe Ile Ile
                85                  90                  95
Glu Tyr Phe His Ser Phe Asp Glu Pro Ala Val Ile Tyr Ser Ser Asn
            100                 105                 110
Gly Asn Lys Thr Lys Trp Leu Arg Tyr Ala Ser Trp Leu Leu Thr Cys
        115                 120                 125
Pro Val Ile Leu Ile Arg Leu Ser Asn Leu Thr Gly Leu Ala Asn Asp
    130                 135                 140
Tyr Asn Lys Arg Thr Met Gly Leu Leu Val Ser Asp Ile Gly Thr Ile
145                 150                 155                 160
Val Trp Gly Thr Thr Ala Ala Leu Ser Lys Gly Tyr Val Arg Val Ile
                165                 170                 175
Phe Phe Leu Met Gly Leu Cys Tyr Gly Ile Tyr Thr Phe Phe Asn Ala
            180                 185                 190
Ala Lys Val Tyr Ile Glu Ala Tyr His Thr Val Pro Lys Gly Arg Cys
        195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Lys Tyr Gly Ser Asn Val Gly His Thr Ile Ile Asp Leu Met Ser
                245                 250                 255
Lys Gln Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ala
            290                 295                 300
Glu Ala Gly Ala Val Ala Ala Ala Lys Ser Arg Ile Thr Ser Glu Gly
```

-continued

```
305                 310                 315                 320
Glu Tyr Ile Pro Leu Asp Gln Ile Asp Ile Asn Val Phe Cys Tyr Glu
                325                 330                 335

Asn Glu Val

<210> SEQ ID NO 78
<211> LENGTH: 310
<212> TYPE: PRT
<213> ORGANISM: Artificial sequence
<220> FEATURE:
<223> OTHER INFORMATION: synthetic sequence

<400> SEQUENCE: 78

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
                100                 105                 110

Gly His Arg Val Lys Trp Leu Arg Tyr Ala Ser Trp Leu Leu Thr Cys
            115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 79
```

<211> LENGTH: 340
<212> TYPE: PRT
<213> ORGANISM: Artificial sequence
<220> FEATURE:
<223> OTHER INFORMATION: synthetic sequence

<400> SEQUENCE: 79

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ser Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Ser Met Val Lys Val Ile Leu
                85                  90                  95

Glu Phe Phe Phe Ser Phe Lys Asn Pro Ser Met Leu Tyr Leu Ala Thr
            100                 105                 110

Gly His Arg Val Lys Trp Leu Arg Tyr Ala Ser Trp Leu Leu Thr Cys
        115                 120                 125

Pro Val Ile Leu Ile Arg Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Lys Tyr Gly Ser Asn Val Gly His Thr Ile Ile Asp Leu Met Ser
                245                 250                 255

Lys Gln Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro Ala Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340

<210> SEQ ID NO 80
<211> LENGTH: 344
<212> TYPE: PRT
<213> ORGANISM: Artificial sequence
<220> FEATURE:
<223> OTHER INFORMATION: synthetic sequence

<400> SEQUENCE: 80

```
Met Ser Arg Arg Pro Trp Leu Leu Ala Leu Ala Leu Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340
```

<210> SEQ ID NO 81
<211> LENGTH: 374
<212> TYPE: PRT
<213> ORGANISM: Artificial sequence
<220> FEATURE:
<223> OTHER INFORMATION: synthetic sequence

<400> SEQUENCE: 81

```
Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Ser Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Ser Met Ile Lys Phe Ile Ile Glu Tyr Phe His Ser Phe Asp Glu Pro
    130                 135                 140

Ala Val Ile Tyr Ser Ser Asn Gly Asn Lys Thr Lys Trp Leu Arg Tyr
145                 150                 155                 160

Ala Ser Trp Leu Leu Thr Cys Pro Val Leu Leu Ile Arg Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
        195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Lys Tyr Gly Ser Asn Ile Gly His
        275                 280                 285

Ser Ile Leu Asp Leu Ile Ala Lys Gln Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp Ala Ala Lys Ser Arg Ile Thr
            340                 345                 350

Ser Glu Gly Glu Tyr Ile Pro Leu Asp Gln Ile Asp Ile Asn Val Phe
        355                 360                 365

Cys Tyr Glu Asn Glu Val
    370
```

<210> SEQ ID NO 82
<211> LENGTH: 305
<212> TYPE: PRT
<213> ORGANISM: Artificial sequence
<220> FEATURE:
<223> OTHER INFORMATION: synthetic sequence

<400> SEQUENCE: 82

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Ile Ser Phe Ala Leu Ser Ala
        50                  55                  60

Leu Cys Leu Met Phe Tyr Gly Tyr Gln Thr Trp Lys Ser Thr Cys Gly
65                  70                  75                  80

Trp Glu Glu Ile Tyr Val Ala Thr Ile Ser Met Ile Lys Phe Ile Ile
                85                  90                  95

Glu Tyr Phe His Ser Phe Asp Glu Pro Ala Val Ile Tyr Ser Ser Asn
            100                 105                 110

Gly Asn Lys Thr Lys Trp Leu Arg Tyr Ala Ser Trp Leu Leu Thr Cys
        115                 120                 125

Pro Val Leu Leu Ile Arg Leu Ser Asn Leu Thr Gly Leu Lys Asp Asp
    130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
            180                 185                 190

Ala Lys Val Tyr Ile Glu Ala Phe His Thr Val Pro Lys Gly Ile Cys
        195                 200                 205

Arg Glu Leu Val Arg Val Met Ala Trp Thr Phe Phe Val Ala Trp Gly
    210                 215                 220

Met Phe Pro Val Leu Phe Leu Leu Gly Thr Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
            260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
    290                 295                 300

Asp
305

<210> SEQ ID NO 83
<211> LENGTH: 335
<212> TYPE: PRT
<213> ORGANISM: Artificial sequence
<220> FEATURE:
<223> OTHER INFORMATION: synthetic sequence

<400> SEQUENCE: 83

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly

```
            20                  25                  30
Gln Cys Phe Cys Leu Ala Trp Leu Lys Ser Asn Gly Thr Asn Ala Glu
        35                  40                  45
Lys Leu Ala Ala Asn Ile Leu Gln Trp Ile Ser Phe Ala Leu Ser Ala
 50                  55                  60
Leu Cys Leu Met Phe Tyr Gly Tyr Gln Thr Trp Lys Ser Thr Cys Gly
 65                  70                  75                  80
Trp Glu Glu Ile Tyr Val Ala Thr Ile Ser Met Ile Lys Phe Ile Ile
                85                  90                  95
Glu Tyr Phe His Ser Phe Asp Glu Pro Ala Val Ile Tyr Ser Ser Asn
            100                 105                 110
Gly Asn Lys Thr Lys Trp Leu Arg Tyr Ala Ser Trp Leu Leu Thr Cys
        115                 120                 125
Pro Val Leu Leu Ile Arg Leu Ser Asn Leu Thr Gly Leu Lys Asp Asp
 130                 135                 140
Tyr Ser Lys Arg Thr Met Gly Leu Leu Val Ser Asp Val Gly Cys Ile
145                 150                 155                 160
Val Trp Gly Ala Thr Ser Ala Met Cys Thr Gly Trp Thr Lys Ile Leu
                165                 170                 175
Phe Phe Leu Ile Ser Leu Ser Tyr Gly Met Tyr Thr Tyr Phe His Ala
            180                 185                 190
Ala Lys Val Tyr Ile Glu Ala Phe His Thr Val Pro Lys Gly Ile Cys
        195                 200                 205
Arg Glu Leu Val Arg Val Met Ala Trp Thr Phe Phe Val Ala Trp Gly
 210                 215                 220
Met Phe Pro Val Leu Phe Leu Leu Gly Thr Glu Gly Phe Gly His Ile
225                 230                 235                 240
Ser Lys Tyr Gly Ser Asn Ile Gly His Ser Ile Leu Asp Leu Ile Ala
                245                 250                 255
Lys Gln Met Trp Gly Val Leu Gly Asn Tyr Leu Arg Val Lys Ile His
            260                 265                 270
Glu His Ile Leu Leu Tyr Gly Asp Ile Arg Lys Lys Gln Lys Ile Thr
        275                 280                 285
Ile Ala Gly Gln Glu Met Glu Val Glu Thr Leu Val Ala Glu Glu Glu
 290                 295                 300
Asp Ala Ala Ala Lys Ser Arg Ile Thr Ser Glu Gly Glu Tyr Ile Pro
305                 310                 315                 320
Leu Asp Gln Ile Asp Ile Asn Val Phe Cys Tyr Glu Asn Glu Val
                325                 330                 335

<210> SEQ ID NO 84
<211> LENGTH: 350
<212> TYPE: PRT
<213> ORGANISM: Artificial sequence
<220> FEATURE:
<223> OTHER INFORMATION: synthetic sequence

<400> SEQUENCE: 84

Met Val Ser Arg Arg Pro Trp Leu Leu Ala Leu Ala Leu Ala Val Ala
 1               5                  10                  15
Leu Ala Ala Gly Ser Ala Gly Ala Ser Thr Gly Ser Asp Ala Thr Val
                20                  25                  30
Pro Val Ala Thr Gln Asp Gly Pro Asp Tyr Val Phe His Arg Ala His
            35                  40                  45
Glu Arg Met Leu Phe Gln Thr Ser Tyr Thr Leu Glu Asn Asn Gly Ser
```

```
            50                  55                  60
Val Ile Cys Ile Pro Asn Asn Gly Gln Cys Phe Cys Leu Ala Trp Leu
 65                  70                  75                  80

Lys Ser Asn Gly Thr Asn Ala Glu Lys Leu Ala Ala Asn Ile Leu Gln
                 85                  90                  95

Trp Val Ser Phe Ala Leu Ser Val Ala Cys Leu Gly Trp Tyr Ala Tyr
            100                 105                 110

Gln Ala Trp Arg Ala Thr Cys Gly Trp Glu Glu Val Tyr Val Ala Leu
        115                 120                 125

Ile Ser Met Met Lys Ser Ile Ile Glu Ala Phe His Ser Phe Asp Ser
    130                 135                 140

Pro Ala Thr Leu Trp Leu Ser Ser Gly Asn Gly Val Lys Trp Met Arg
145                 150                 155                 160

Tyr Gly Ser Trp Leu Leu Thr Cys Pro Val Ile Leu Ile Arg Leu Ser
                165                 170                 175

Asn Leu Thr Gly Leu Lys Asp Asp Tyr Ser Lys Arg Thr Met Gly Leu
            180                 185                 190

Leu Val Ser Asp Val Gly Cys Ile Val Trp Gly Ala Thr Ser Ala Met
        195                 200                 205

Cys Thr Gly Trp Thr Lys Ile Leu Phe Phe Leu Ile Ser Leu Ser Tyr
    210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                245                 250                 255

Trp Leu Phe Phe Val Ser Trp Gly Met Phe Pro Val Leu Phe Leu Leu
            260                 265                 270

Gly Pro Glu Gly Phe Gly His Ile Ser Lys Tyr Gly Ser Asn Ile Gly
        275                 280                 285

His Ser Ile Leu Asp Leu Ile Ala Lys Gln Met Trp Gly Val Leu Gly
    290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser
            340                 345                 350

<210> SEQ ID NO 85
<211> LENGTH: 380
<212> TYPE: PRT
<213> ORGANISM: Artificial sequence
<220> FEATURE:
<223> OTHER INFORMATION: synthetic sequence

<400> SEQUENCE: 85

Met Val Ser Arg Arg Pro Trp Leu Leu Ala Leu Ala Leu Ala Val Ala
 1               5                  10                  15

Leu Ala Ala Gly Ser Ala Gly Ala Ser Thr Gly Ser Asp Ala Thr Val
                20                  25                  30

Pro Val Ala Thr Gln Asp Gly Pro Asp Tyr Val Phe His Arg Ala His
            35                  40                  45

Glu Arg Met Leu Phe Gln Thr Ser Tyr Thr Leu Glu Asn Asn Gly Ser
        50                  55                  60

Val Ile Cys Ile Pro Asn Asn Gly Gln Cys Phe Cys Leu Ala Trp Leu
```

```
                65                  70                  75                  80
Lys Ser Asn Gly Thr Asn Ala Glu Lys Leu Ala Ala Asn Ile Leu Gln
                    85                  90                  95

Trp Val Ser Phe Ala Leu Ser Val Ala Cys Leu Gly Trp Tyr Ala Tyr
                100                 105                 110

Gln Ala Trp Arg Ala Thr Cys Gly Trp Glu Val Tyr Val Ala Leu
                115                 120                 125

Ile Ser Met Met Lys Ser Ile Ile Glu Ala Phe His Ser Phe Asp Ser
            130                 135                 140

Pro Ala Thr Leu Trp Leu Ser Gly Asn Gly Val Lys Trp Met Arg
145                 150                 155                 160

Tyr Gly Ser Trp Leu Leu Thr Cys Pro Val Ile Leu Ile Arg Leu Ser
                    165                 170                 175

Asn Leu Thr Gly Leu Lys Asp Asp Tyr Ser Lys Arg Thr Met Gly Leu
                180                 185                 190

Leu Val Ser Asp Val Gly Cys Ile Val Trp Gly Ala Thr Ser Ala Met
                195                 200                 205

Cys Thr Gly Trp Thr Lys Ile Leu Phe Phe Leu Ile Ser Leu Ser Tyr
        210                 215                 220

Gly Met Tyr Thr Tyr Phe His Ala Ala Lys Val Tyr Ile Glu Ala Phe
225                 230                 235                 240

His Thr Val Pro Lys Gly Leu Cys Arg Gln Leu Val Arg Ala Met Ala
                    245                 250                 255

Trp Leu Phe Phe Val Ser Trp Gly Met Phe Pro Val Leu Phe Leu Leu
                260                 265                 270

Gly Pro Glu Gly Phe Gly His Ile Ser Lys Tyr Gly Ser Asn Ile Gly
            275                 280                 285

His Ser Ile Leu Asp Leu Ile Ala Lys Gln Met Trp Gly Val Leu Gly
        290                 295                 300

Asn Tyr Leu Arg Val Lys Ile His Glu His Ile Leu Leu Tyr Gly Asp
305                 310                 315                 320

Ile Arg Lys Lys Gln Lys Ile Thr Ile Ala Gly Gln Glu Met Glu Val
                325                 330                 335

Glu Thr Leu Val Ala Glu Glu Asp Lys Tyr Glu Ser Ser Ala Ala
                340                 345                 350

Ala Lys Ser Arg Ile Thr Ser Glu Gly Glu Tyr Ile Pro Leu Asp Gln
            355                 360                 365

Ile Asp Ile Asn Val Phe Cys Tyr Glu Asn Glu Val
            370                 375                 380

<210> SEQ ID NO 86
<211> LENGTH: 310
<212> TYPE: PRT
<213> ORGANISM: Artificial sequence
<220> FEATURE:
<223> OTHER INFORMATION: synthetic sequence

<400> SEQUENCE: 86

Met Asp Tyr Gly Gly Ala Leu Ser Ala Val Gly Leu Phe Gln Thr Ser
1               5                   10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
```

```
                 50                  55                  60

Ala Cys Leu Gly Trp Tyr Ala Tyr Gln Ala Trp Arg Ala Thr Cys Gly
 65                  70                  75                  80

Trp Glu Glu Val Tyr Val Ala Leu Ile Ser Met Met Lys Ser Ile Ile
                     85                  90                  95

Glu Ala Phe His Ser Phe Asp Ser Pro Ala Thr Leu Trp Leu Ser Ser
                    100                 105                 110

Gly Asn Gly Val Lys Trp Met Arg Tyr Gly Ser Trp Leu Leu Thr Cys
                115                 120                 125

Pro Val Ile Leu Ile Arg Leu Ser Asn Leu Thr Gly Leu Lys Asp Asp
            130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                    165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Leu Cys
            195                 200                 205

Arg Gln Leu Val Arg Ala Met Ala Trp Leu Phe Phe Val Ser Trp Gly
        210                 215                 220

Met Phe Pro Val Leu Phe Leu Gly Pro Glu Gly Phe Gly His Ile
225                 230                 235                 240

Ser Lys Tyr Gly Ser Asn Ile Gly His Ser Ile Leu Asp Leu Ile Ala
                    245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Gln Lys Ile Thr
            275                 280                 285

Ile Ala Gly Gln Glu Met Glu Val Glu Thr Leu Val Ala Glu Glu Glu
        290                 295                 300

Asp Lys Tyr Glu Ser Ser
305                 310

<210> SEQ ID NO 87
<211> LENGTH: 340
<212> TYPE: PRT
<213> ORGANISM: Artificial sequence
<220> FEATURE:
<223> OTHER INFORMATION: synthetic sequence

<400> SEQUENCE: 87

Met Asp Tyr Gly Gly Ala Leu Ser Ala Val Gly Leu Phe Gln Thr Ser
 1               5                  10                  15

Tyr Thr Leu Glu Asn Asn Gly Ser Val Ile Cys Ile Pro Asn Asn Gly
                20                  25                  30

Gln Cys Phe Cys Leu Ala Trp Leu Lys Ser Asn Gly Thr Asn Ala Glu
            35                  40                  45

Lys Leu Ala Ala Asn Ile Leu Gln Trp Val Ser Phe Ala Leu Ser Val
 50                  55                  60

Ala Cys Leu Gly Trp Tyr Ala Tyr Gln Ala Trp Arg Ala Thr Cys Gly
 65                  70                  75                  80

Trp Glu Glu Val Tyr Val Ala Leu Ile Ser Met Met Lys Ser Ile Ile
                     85                  90                  95

Glu Ala Phe His Ser Phe Asp Ser Pro Ala Thr Leu Trp Leu Ser Ser
```

```
                        100                 105                 110
Gly Asn Gly Val Lys Trp Met Arg Tyr Gly Ser Trp Leu Leu Thr Cys
        115                 120                 125

Pro Val Ile Leu Ile Arg Leu Ser Asn Leu Thr Gly Leu Lys Asp Asp
        130                 135                 140

Tyr Ser Lys Arg Thr Met Gly Leu Leu Val Ser Asp Val Gly Cys Ile
145                 150                 155                 160

Val Trp Gly Ala Thr Ser Ala Met Cys Thr Gly Trp Thr Lys Ile Leu
                165                 170                 175

Phe Phe Leu Ile Ser Leu Ser Tyr Gly Met Tyr Thr Tyr Phe His Ala
                180                 185                 190

Ala Lys Val Tyr Ile Glu Ala Phe His Thr Val Pro Lys Gly Leu Cys
        195                 200                 205

Arg Gln Leu Val Arg Ala Met Ala Trp Leu Phe Phe Val Ser Trp Gly
        210                 215                 220

Met Phe Pro Val Leu Phe Leu Leu Gly Pro Glu Gly Phe Gly His Ile
225                 230                 235                 240

Ser Lys Tyr Gly Ser Asn Ile Gly His Ser Ile Leu Asp Leu Ile Ala
                245                 250                 255

Lys Gln Met Trp Gly Val Leu Gly Asn Tyr Leu Arg Val Lys Ile His
                260                 265                 270

Glu His Ile Leu Leu Tyr Gly Asp Ile Arg Lys Lys Gln Lys Ile Thr
        275                 280                 285

Ile Ala Gly Gln Glu Met Glu Val Glu Thr Leu Val Ala Glu Glu Glu
        290                 295                 300

Asp Lys Tyr Glu Ser Ser Ala Ala Ala Lys Ser Arg Ile Thr Ser Glu
305                 310                 315                 320

Gly Glu Tyr Ile Pro Leu Asp Gln Ile Asp Ile Asn Val Phe Cys Tyr
                325                 330                 335

Glu Asn Glu Val
            340
```